US012590087B2

(12) United States Patent
Han et al.

(10) Patent No.: US 12,590,087 B2
(45) Date of Patent: Mar. 31, 2026

(54) INHIBITING USP36

(71) Applicant: Valo Health, Inc., Lexington, MA (US)

(72) Inventors: Bingsong Han, Boston, MA (US); Katherine Kayser-Bricker, Boston, MA (US); Cuixian Liu, Boston, MA (US)

(73) Assignee: Valo Health, Inc., Lexington, MA (US)

( * ) Notice: Subject to any disclaimer, the term of this patent is extended or adjusted under 35 U.S.C. 154(b) by 1017 days.

(21) Appl. No.: 17/607,595

(22) PCT Filed: Apr. 30, 2020

(86) PCT No.: PCT/US2020/030833

§ 371 (c)(1),
(2) Date: Oct. 29, 2021

(87) PCT Pub. No.: WO2020/223548

PCT Pub. Date: Nov. 5, 2020

(65) Prior Publication Data

US 2022/0213088 A1 Jul. 7, 2022

Related U.S. Application Data

(60) Provisional application No. 62/840,737, filed on Apr. 30, 2019.

(51) Int. Cl.

*C07D 417/14* (2006.01)
*C07D 277/46* (2006.01)
*C07D 285/06* (2006.01)
*C07D 417/12* (2006.01)

(52) U.S. Cl.

CPC ......... *C07D 417/14* (2013.01); *C07D 277/46* (2013.01); *C07D 285/06* (2013.01); *C07D 417/12* (2013.01)

(58) Field of Classification Search

None
See application file for complete search history.

(56) References Cited

U.S. PATENT DOCUMENTS 7,531,531 B2 * 5/2009 Fancelli .................. A61P 25/28 514/215
2009/0163545 A1 6/2009 Goldfarb
2016/0289191 A1 10/2016 Dales et al.

FOREIGN PATENT DOCUMENTS

CN 105878244 A * 8/2016
JP 2004521924 A 7/2004
JP 2011525896 A 9/2011
WO 1991017979 11/1991
WO 2002070483 A1 9/2002
WO 2016134026 A1 8/2016
WO 2018057618 A1 3/2018
WO 2023061051 A1 4/2023

OTHER PUBLICATIONS

Yang et al., ACS Combinatorial Science 2016 18 (8), 499-506, Supplemental Information (Year: 2016).*
CAS RN 955722-22-2,entered Nov. 23, 2007 (Year: 2007).*
Office Action for Chinese Patent ZL202080041237.8, 7 pages.
Davis et al., "Small Molecule Inhibition of the Ubiquitin-specific Protease USP2 Accelerates cyclin D1 Degradation and Leads to Cell Cycle Arrest in Colorectal Cancer and Mantle Cell Lymphoma Models", Journal of Biological Chemistry, Nov. 18, 2016, pp. 24628-24640, vol. 291, No. 47.
European Search Report and Opinion for European Application EP 20799375.9, Dec. 14, 2022, 5 pages.
Hu et al., "Discovery of novel inhibitors of human galactokinase by virtual screening", Journal of Computer-Aided Molecular Design, Apr. 2019, pp. 405-417, vol. 33, No. 4.
International Search Report for PCT Application PCT/US2020/030833, Sep. 3, 2020, 11, pages.
Japanese Search Report for Japanese Application 2021-56341, Feb. 28, 2024, 29 pages.
Japanese Notice of Reasons for Refusal for Japanese Application 2021-56341, Apr. 22, 2024,3 pages.
Japanese Notice of Reasons for Refusal for Japanese Application 2021-56341, Oct. 24, 2024, 3 pages.
CAS Registry 380167-69-1, STN, https://www.stn.org/stn/#, Jan. 2, 2022, 1 page.
PubChem CID 835810, Jul. 9, 2005, 15 pages.

* cited by examiner

*Primary Examiner* — Jeffrey S Lundgren
*Assistant Examiner* — Anthony Joseph Seitz
(74) *Attorney, Agent, or Firm* — Barnes & Thornburg LLP; Aisha R. Hasan; Ryan L. Marshall

(57) ABSTRACT

The present disclosure is directed to compounds of formulas (I)-(VI), which are useful as modulators of USP36. The compounds are further useful in the inhibition of USP36 and the treatment of diseases or disorders associated with the inhibition of USP36. For instance, the disclosure is concerned with compounds and compositions for inhibition of USP36, methods of treating diseases associated with the inhibition of USP36 (e.g., certain forms of cancer), and methods of synthesis of these compounds.

11 Claims, No Drawings

INHIBITING USP36

CROSS REFERENCE TO RELATED APPLICATIONS

This application is a National Stage application of International Application No. PCT/US2020/030833, filed Apr. 30, 2020, which claims the benefit of U.S. Provisional Application No. 62/840,737, filed Apr. 30, 2019, each of which is incorporated by reference herein in its entirety.

TECHNICAL FIELD

The present disclosure relates to compounds useful for the inhibition of ubiquitin specific peptidase 36 (USP36) and methods of their preparation. Inhibitors of USP36 are useful for the treatment of several forms of cancer.

BACKGROUND

Aggressive cancers, including subtypes of pancreatic, colorectal, lung, brain, ovarian, and prostate cancers, are characterized mainly by rapid tumor formation, growth, and spread. They often present substantial challenges with regards to effective treatments and are particularly susceptible to developing resistance, such that therapeutic options are exhausted relatively quickly and prognoses are typically poor. Aggressive cancers present a critical unmet medical need and an opportunity for development of therapies that can selectively target rapidly proliferating cancer cells while maintaining a favorable therapeutic margin.

Cell proliferation consumes a substantial amount of energy, particularly for activities in the nucleolus. These include transcription and assembly of ribosomal RNA (rRNA), ribosomal biogenesis, cell cycle progression, DNA replication and repair, stress signaling, and cell survival. As cell proliferation rates increase, a state of nucleolar stress results where upregulation of ribosomal biogenesis and elevations in associated metabolic resources are essential to maintain nucleolar integrity. A loss of integrity interferes with the cell replication process and can promote cell death. This connection between ribosomal biogenesis, nucleolar integrity, and cell viability can be exploited as a mechanism for chemotherapeutics, and suggests that cells with the highest levels of nucleolar stress may be differentially impacted. Nearly all cancer cell types show evidence of nucleolar stress with larger and/or elevated numbers of nucleoli, and nucleolar size can sometimes be a prognostic indicator of clinical outcome. This is consistent with findings that show higher proliferation rates, a hallmark characteristic of aggressive cancers, are associated with signs of greater nucleolar stress. Furthermore, differential rates of proliferation are reflected in the substantial variability in ribosomal biogenesis across cancer types. Rapid cell proliferation rates are associated with increasing levels of ribosomal biogenesis hyperactivation. Given that aggressive cancer cells are characterized by their rapid division, they are typically in a relatively high state of nucleolar stress with substantially elevated metabolic needs, and may be particularly vulnerable to perturbations in ribosome production. Therefore, aggressive cancers are an appropriate target for therapeutic inhibition of ribosomal biogenesis.

Further, this pathway may provide selective cytoxicity for cancer cells with lower risk of broad genotoxicity typical of many other cancer treatments. Ribosomal biogenesis and nucleolar integrity can be affected through inhibition of USP36. It is a deubiquitinase (DUB) known to be overexpressed in many human cancers, including subsets of breast, lung, and ovarian cancers. USP36 supports ribosomal biogenesis and nucleolar integrity through deubiquitylation of a plethora of nucleolar proteins (eg, c-MYC, DHX33, and RNA Pol 1) and stabilization against ubiquitylation-mediated proteasomal degradation.

The DUB activity of USP36 on nucleolar MYC may be an important component of the therapeutic effects, as it is known that tight regulation of MYC levels is essential for normal cell growth and proliferation. MYC controls the expression of most, if not all, actively transcribed genes in the human genome and coordinates many cellular processes. It plays a direct role in ribosome biogenesis, RNA transcription, and protein synthesis, and shows enriched localization in the nucleolus. Notably, pathological activation or overexpression of MYC contributes to development of malignancies. The ubiquitination status-dependent regulation of MYC stability and activity involves a multitude of enzymes, including USP36. MYC levels are significantly reduced with USP36 knockdown and this change is associated with inhibited cell proliferation. This is consistent with a well-accepted view that high MYC activity-induced ribosome biogenesis is an essential part of cell growth and tumorigenesis. Reduced ribosome production due to USP36 inhibition would be expected to counter MYC-induced nucleolar hyperactivity and render the cell deficient in the resources needed to sustain proliferation. Also, USP36 is a target gene of MYC, suggesting a positive feedback regulatory loop.

SUMMARY

Compounds of formula (I) are disclosed:

(I)

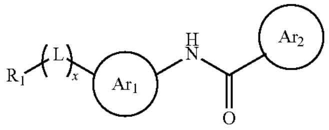

and pharmaceutically acceptable salts, hydrates, solvates, isomers, and tautomers thereof, wherein:

$R_1$ is selected from:

$(C_1\text{-}C_4)$ alkyl optionally substituted with 1-3 $R_2$, $(C_3\text{-}C_6)$ cycloalkyl optionally substituted with one $R_3$, aryl optionally substituted with 1-2 $R_4$, heteroaryl substituted with one $R_5$, bicyclic heteroaryl optionally substituted with one $(C_1\text{-}C_4)$ alkyl, partially saturated bicyclyl optionally substituted with one halogen, and

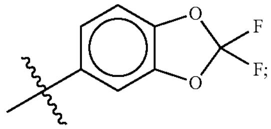;

each $R_2$ is independently selected from:
($C_1$-$C_4$) alkyl,
($C_3$-$C_6$) cycloalkyl,
($C_6$-$C_{12}$) spirocycloalkyl,
aryl optionally substituted with one halogen or —$OR_6$, and
3-6 membered heterocyclyl;
$R_3$ is ($C_1$-$C_4$) alkyl;
each $R_4$ is independently selected from ($C_1$-$C_4$) alkyl optionally substituted with halogen, —$OR_6$, halogen, and 3-6 membered heterocyclyl;
$R_5$ is aryl substituted with one halogen;
$R_6$ is selected from aryl, and ($C_1$-$C_4$) alkyl optionally substituted with halogen;
L is —NHC(O)—;
x is zero or one;
$Ar_1$ is a heteroaryl or bicyclic heteroaryl and is optionally substituted with one ($C_1$-$C_4$) alkyl;
$Ar_2$ is an aryl or heteroaryl, optionally substituted with 1-2 $R_7$;
each $R_7$ is independently selected from: aryl, halogen, trifluoromethyl, and —$NHS(O)_2R_8$;
$R_8$ is aryl optionally substituted with one $R_9$; and
$R_9$ is halogen or aryl.

with the provisos that:
(i) if $Ar_2$ has 0-1 substituents, $Ar_1$ is not thiazolyl; and
(ii) the compound is not:

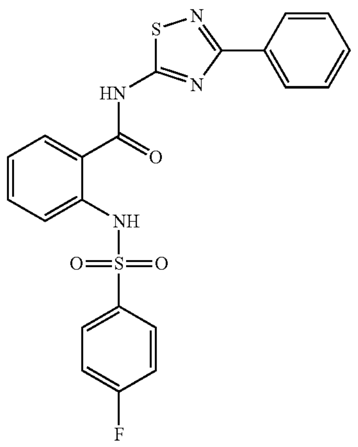

2-((4-fluorophenyl)sulfonamido)-N-(3-phenyl-1,2,4-thiadiazol-5-yl)benzamide .

In another aspect, a method of treating, preventing, inhibiting, or eliminating a disease or disorder associated with the activity of USP36 in a patient is disclosed which includes administering to the patient in need thereof, a therapeutically effective amount of the foregoing compounds or pharmaceutical compositions thereof.

DETAILED DESCRIPTION

The present disclosure relates to compounds that are capable of modulating the activity of ubiquitin specific peptidase 36 (USP36). The disclosure features methods of treating, preventing, or ameliorating a disease or disorder in which USP36 plays a role by administering to a patient in need thereof a therapeutically effective amount of a compound of any one of formulas (I)-(VI), or a pharmaceutically acceptable salt thereof. The methods of the present disclosure can be used in the treatment of a variety of USP36-dependent diseases and disorders by inhibiting the activity of USP36. Inhibition of USP36 provides a novel approach to the treatment of diseases including, but not limited to, certain forms of cancer.

Definitions

The articles “a” and “an” are used in this disclosure to refer to one or more than one (e.g., to at least one) of the grammatical object of the article. By way of example, “an element” means one element or more than one element.

The term “and/or” is used in this disclosure to mean either “and” or “or” unless indicated otherwise.

The term “optionally substituted” is understood to mean that a given chemical moiety can (but is not required to) be bonded to other substituents. Unless otherwise specifically defined, optional substituents bond to the chemical moiety with any chemically feasible regiochemistry and/or stereochemistry (where applicable). For instance, an alkyl group that is optionally substituted can be a fully saturated alkyl chain (e.g., a pure hydrocarbon). Alternatively, the same optionally substituted alkyl group can have substituents in place of one or more hydrogen atoms. For instance, it can be bonded, at any point along the chain, to any recited optional substituent. Thus, the term “optionally substituted” means that a given chemical moiety has the potential to contain other functional groups, but does not necessarily have any further functional groups. “Optionally substituted” as used herein also refers to substituted or unsubstituted whose meaning is described below.

As used herein, the term “substituted” means that the specified group or moiety bears one or more of the recited substituents, wherein the substituents may connect to the specified group or moiety at one position. Unless otherwise specifically defined, substituents may be bonded to the chemical moiety with any chemically feasible regiochemistry and/or stereochemistry (where applicable).

As used herein, the term “unsubstituted” means that the specified group bears no substituents.

As used herein, the term “aryl” refers to monocyclic, aromatic hydrocarbon groups that have one aromatic ring having a total of 5 to 14 ring atoms, such as, for example, phenyl. Unless otherwise specifically defined, “aryl” groups are unsubstituted.

As used herein, the term “heteroaryl” refers to a monocyclic aromatic radical of 5 to 14 ring atoms, containing one or more ring heteroatoms selected from the group consisting of N, O, and S, the remaining ring atoms being C. Examples include, but are not limited to, furyl, thienyl, pyrrolyl, pyridinyl, pyrazolyl, pyrimidinyl, imidazolyl, isoxazolyl, oxazolyl, oxadiazolyl, pyrazinyl, thiophen-2-yl, isothiazolyl, thiazolyl, thiadiazolyl, triazolyl, triazinyl. Unless otherwise specifically defined, “heteroaryl” groups are unsubstituted.

As used herein, the term “bicyclic heteroaryl” means a bicyclic aromatic radical, containing one or more ring heteroatoms selected from the group consisting of N, O, and S, the remaining ring atoms being C. Examples include, but are not limited to, indolyl, quinolyl, benzopyranyl, indazolyl, benzimidazolyl, thieno[3,2-b]thiophene, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, 6,7-dihydro-4H-thieno[3.2-c]pyran. Unless otherwise specifically defined, "bicyclic heteroaryl" groups are unsubstituted.

As used herein, the terms "halogen" or "halo" refers to fluorine (i.e. "F" or "fluoro"), chlorine (i.e. "Cl" or "chloro"), bromine (i.e. "Br" or "bromo"), or iodine (i.e. "I" or "iodo").

As used herein, the term "($C_1$-$C_4$) alkyl" refers to a straight or branched chain saturated hydrocarbon containing 1-4 carbon atoms. Examples of a ($C_1$-$C_4$) alkyl group include, but are not limited to, methyl, ethyl, propyl, butyl, isopropyl, isobutyl, sec-butyl, tert-butyl. "$C_1$ alkyl" refers to an alkyl chain containing 1 carbon atom, e.g. methyl. "$C_2$ alkyl" refers to an alkyl chain containing 2 carbon atoms, e.g. ethyl. "$C_3$ alkyl" refers to an alkyl chain containing 3 carbon atoms, e.g. propyl or isopropyl. "$C_4$ alkyl" refers to an alkyl chain containing 4 carbon atoms, e.g. butyl, isobutyl, sec-butyl, or tert-butyl. Unless otherwise specifically defined, "($C_1$-$C_4$) alkyl" groups are unsubstituted.

As used herein, the term "($C_3$-$C_6$) cycloalkyl" refers to a monocyclic saturated ring containing 3-6 carbon atoms. Examples of cycloalkyl groups include, without limitations, cyclopropyl, cyclobutyl, cyclopentyl, cyclohexyl. "$C_3$ cycloalkyl" refers to a cycloalkyl containing 3 carbon atoms, e.g. cyclopropyl. "$C_4$ cycloalkyl" refers to a cycloalkyl containing 4 carbon atoms, e.g. cyclobutyl. "$C_5$ cycloalkyl" refers to a cycloalkyl containing 5 carbon atoms, e.g. cyclopentyl. "$C_6$ cycloalkyl" refers to a cycloalkyl containing 6 carbon atoms, e.g. cyclohexyl. Unless otherwise specifically defined, "($C_3$-$C_6$) cycloalkyl" groups are unsubstituted.

As used herein, the term "3-6 membered heterocyclyl" refers to a monocyclic ring containing a total of 3 to 6 carbon and heteroatoms taken from oxygen, nitrogen, or sulfur, where such rings are either saturated or partially unsaturated. Examples of heterocyclyl rings include, but are not limited to, oxetanyl, azetidinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, morpholinyl, thiomorpholinyl, thiomorpholinyl S-oxide, thiomorpholinyl S-dioxide, piperazinyl, and oxazolidinonyl. Unless otherwise specifically defined, "3-6 membered heterocyclyl" groups are unsubstituted.

As used herein, the term "partially saturated bicyclyl" refers to a bicyclic ring moiety composed of 6-12 C atoms, wherein an unsaturated, or partially saturated, ring is fused with a fully unsaturated ring. Examples of partially saturated bicyclyl moieties include, but are not limited to indanyl and tetrahydronaphthalenyl. Unless otherwise specifically defined, "partially saturated bicyclyl" groups are unsubstituted.

As used herein, the term "($C_6$-$C_{12}$) spirocycloalkyl" refers to a bicyclic ring system having 6-12 carbon atoms, wherein the rings are connected to one another through a single atom. The rings can be different in size and nature, or identical in size and nature. Examples include, but are not limited to, spirohexane, spiroheptane, spirooctane, spirononane, spirodecane, spiroundecane, and spirododecane. "$C_6$ spirocycloalkyl" refers to a spirocycloalkyl having 6 carbon atoms, e.g. spirohexane. "$C_7$ spirocycloalkyl" refers to a spirocycloalkyl having 7 carbon atoms, e.g. spiroheptane. "$C_8$ spirocycloalkyl" refers to a spirocycloalkyl having 8 carbon atoms, e.g. spirooctane. "$C_9$ spirocycloalkyl" refers to a spirocycloalkyl having 9 carbon atoms, e.g. spirononane. "$C_{10}$ spirocycloalkyl" refers to a spirocycloalkyl having 10 carbon atoms, e.g. spirodecane. "$C_{11}$ spirocycloalkyl" refers to a spirocycloalkyl having 11 carbon atoms, e.g. spiroundecane. "$C_{12}$ spirocycloalkyl" refers to a spirocycloalkyl having 12 carbon atoms, e.g. spirododecane. Unless otherwise specifically defined, "($C_6$-$C_{12}$) spirocycloalkyl" groups are unsubstituted.

As used herein, the term "isomer" refers to compounds that have the same composition and molecular weight but differ in physical and/or chemical properties. The structural difference may be in constitution (e.g., geometric isomers) or in the ability to rotate a plane of polarized light (stereoisomers). With regard to stereoisomers, the compounds of Formula (I) may have one or more asymmetric carbon atoms and may occur as racemates, racemic mixtures or as individual enantiomers or diastereomers.

The term "pharmaceutical composition" as used herein, refers to a composition in which individual components or ingredients are themselves pharmaceutically acceptable, e.g., where oral administration is foreseen, acceptable for oral use; where topical administration is foreseen, topically acceptable; and where intravenous administration is foreseen, intravenously acceptable.

The term "solvate" refers to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

"Pharmaceutically acceptable salts" are well known in the art. For example, S. M. Berge et al., describe pharmaceutically acceptable salts in detail in J. Pharmaceutical Sciences, 1977, 66, 1-19, incorporated herein by reference. Representative pharmaceutically acceptable salts include, e.g., water-soluble and water-insoluble salts, such as acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methyl sulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. The compounds of formulas (I)-(VI) may form salts which are also within the scope of this disclosure. Reference to a compound of Formula I herein is understood to include reference to salts thereof, unless otherwise indicated.

Novel USP36 inhibitors are provided. Unless otherwise indicated "USP36 Inhibitor Compound" as used herein refers to a compound having a detectable $IC_{50}$ value of 10 micromolar or lower, when tested according to the USP36 inhibition biochemical assay of Example 9 described hereafter. A USP36 Inhibitor Compound of the present disclosure can be dosed at a therapeutically effective level.

A "patient" or "subject" is a mammal, e.g., a human, mouse, rat, guinea pig, dog, cat, horse, cow, pig, or non-human primate, such as a monkey, chimpanzee, baboon, or rhesus.

As used herein, the term "therapeutically effective amount" refers to that amount of the therapeutic agent sufficient to result in amelioration of one or more symptoms of a disorder, or prevent advancement of a disorder, or cause regression of the disorder.

The term "carrier", as used in this disclosure, encompasses carriers, excipients, and diluents and means a material, composition or vehicle, such as a liquid or solid filler, diluent, excipient, solvent, or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound, a pharmaceutically acceptable salt of a disclosed compound or a composition to a subject, a pharmaceutically acceptable salt of a compound, or a composition to a subject, which can form an equivalent amount of active compound within the subject's body.

Compounds of the Disclosure

The present disclosure relates to compounds, or pharmaceutically acceptable salts, hydrates, solvates, tautomers, and isomers thereof, capable of modulating USP36, which are useful for the treatment of diseases and disorders associated with modulation of USP36. The disclosure further relates to compounds, or pharmaceutically acceptable salts, hydrates, solvates, tautomers, and isomers thereof, which are useful for inhibiting USP36.

Unless otherwise indicated herein, all isomeric forms of specified chemical compounds are provided by the present disclosure, including mixtures thereof. All tautomeric forms are also intended to be included.

The compounds of formulas (I)-(VI), unless otherwise indicated, may contain one or more stereocenters, and, therefore, exist in different stereoisomeric forms. It is intended that unless otherwise indicated all stereoisomeric forms of the compounds of formulas (I)-(VI), including enantiomeric forms (which may exist even in the absence of asymmetric carbons), rotameric forms, atropisomers, and diastereomeric forms, as well as mixtures thereof, including racemic mixtures, form part of the present disclosure. In addition, the present disclosure embraces all geometric and positional isomers. For example, if a compound of any one of formulas (I)-(VI) incorporates a double bond or a fused ring, both the cis- and trans-forms, as well as mixtures, are embraced within the scope of the disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry. Individual stereoisomers of the compounds of the disclosure may be, for example, substantially free of other isomers, or may be admixed, for example, as racemates or with all other, or other selected, stereoisomers. In some embodiments of the disclosure, the compounds of formula (I)-(VI) are enantiomers. In some embodiments, the compounds are the (S)-enantiomer. In other embodiments the compounds are the (R)-enantiomer. In some embodiments, the compounds of formulas (I)-(VI) may be (+) or (−) enantiomers.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., a chiral auxiliary such as a chiral alcohol or Mosher's acid chloride), separating the diastereomers and converting (e.g., by hydrolyzing) the individual diastereomers to the corresponding pure enantiomers. Also, some of the compounds of formulas (I)-(VI) may be atropisomers (e.g., substituted biaryls) and are considered as part of this disclosure. Enantiomers can also be separated by use of a chiral HPLC column.

In addition, unless otherwise indicated, the present disclosure embraces all geometric and positional isomers (such as, for example, 4-pyridyl and 3-pyridyl). For example, if a compound of the disclosure incorporates a double bond or a fused ring, both the cis- and trans-forms, as well as mixtures, are embraced within the scope of the disclosure. If the compound contains a double bond, the substituent may be in the E or Z configuration, unless otherwise indicated. If the compound contains a disubstituted cycloalkyl, the cycloalkyl substituent may have a cis- or trans configuration, unless otherwise indicated.

Compounds of the disclosure, and pharmaceutically acceptable salts and stereoisomers, thereof may exist in their tautomeric form (for example, as an amide or imino ether). Moreover, all keto-enol and imine-enamine forms of the compounds are included in the disclosure. All such tautomeric forms are contemplated herein as part of the present disclosure.

The use of the terms "salt" and the like, is intended to equally apply to the salt of enantiomers, stereoisomers, rotamers, tautomers, positional isomers, and racemates of the inventive compounds.

When compounds of the present invention contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, iron (III), iron (II), lithium, magnesium, manganese, potassium, sodium, zinc, and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When compounds of the present invention contain relatively basic functionalities, acid addition salts can be obtained by contacting the neutral form of such compounds with a sufficient amount of the desired acid, either neat or in a suitable inert solvent. Acids suitable for the preparation of pharmaceutically acceptable acid addition salts include acetic, ascorbic, benzenesulfonic, benzoic, camphorsulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic, and the like.

The compounds of formulas (I)-(VI) may form acid addition salts or base addition salts, which may be pharmaceutically acceptable salts.

Compounds of formula (I):

(I)

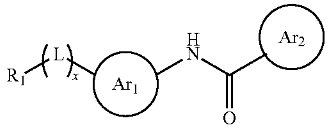

and pharmaceutically acceptable salts, hydrates, solvates, isomers, and tautomers thereof, are disclosed, wherein:

$R_1$ is selected from:
- $(C_1-C_4)$ alkyl optionally substituted with 1-3 $R_2$,
- $(C_3-C_6)$ cycloalkyl optionally substituted with one $R_3$,
- aryl optionally substituted with 1-2 $R_4$,
- heteroaryl substituted with one $R_5$,
- bicyclic heteroaryl optionally substituted with one $(C_1-C_4)$ alkyl,
- partially saturated bicyclyl optionally substituted with one halogen, and

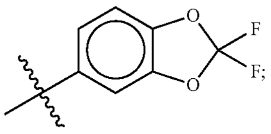

each $R_2$ is independently selected from:
- $(C_1-C_4)$ alkyl,
- $(C_3-C_6)$ cycloalkyl,
- $(C_6-C_{12})$ spirocycloalkyl,
- aryl optionally substituted with one halogen or —$OR_6$, and
- 3-6 membered heterocyclyl;

$R_3$ is $(C_1-C_4)$ alkyl;

each $R_4$ is independently selected from $(C_1-C_4)$ alkyl optionally substituted with halogen, —$OR_6$, halogen, and 3-6 membered heterocyclyl;

$R_5$ is aryl substituted with one halogen;

$R_6$ is selected from aryl, and $(C_1-C_4)$ alkyl optionally substituted with halogen;

L is —NHC(O)—;

x is zero or one;

$Ar_1$ is a heteroaryl or bicyclic heteroaryl and is optionally substituted with one $(C_1-C_4)$ alkyl;

$Ar_2$ is an aryl or heteroaryl, optionally substituted with 1-2 $R_7$;

each $R_7$ is independently selected from: aryl, halogen, trifluoromethyl, and —$NHS(O)_2R_8$;

$R_8$ is aryl optionally substituted with one $R_9$; and $R_9$ is halogen or aryl, with the provisos that:

(i) if $Ar_2$ has 0-1 substituents, $Ar_1$ is not thiazolyl; and (ii) the compound is not:

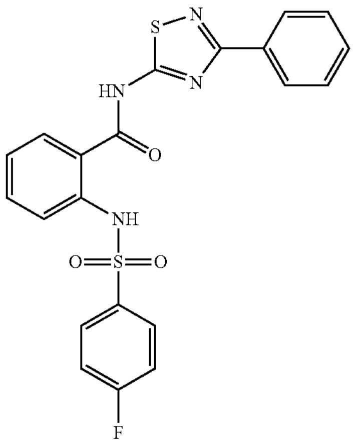 [SMILES: O=C(Nc1nc(-c2ccccc2)ns1)c1ccccc1NS(=O)(=O)c1ccc(F)cc1]

2-((4-fluorophenyl)sulfonamido)-N-(3-phenyl-1,2,4-thiadiazol-5-yl)benzamide.

In some embodiments, compounds of formula (I) are further given by formula (Ia):

(Ia)

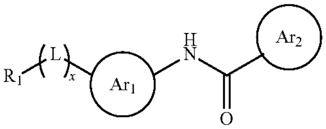

and pharmaceutically acceptable salts, hydrates, solvates, isomers, and tautomers thereof, wherein:

$R_1$ is selected from:
- $(C_1-C_4)$ alkyl optionally substituted with 1-3 $R_2$,
- $(C_3-C_6)$ cycloalkyl optionally substituted with one $R_3$ or fused with an aryl to form a bicyclyl optionally substituted with one halogen,
- aryl optionally substituted with 1-2 $R_4$,
- heteroaryl substituted with one $R_5$,
- bicyclic heteroaryl optionally substituted with one $(C_1-C_4)$ alkyl,
- partially saturated bicyclyl, and

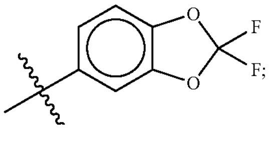

$R_2$ is selected from:

($C_1$-$C_4$) alkyl, ($C_3$-$C_6$) cycloalkyl optionally fused with a ($C_3$-$C_6$) cycloalkyl to form a spirocycle, aryl optionally substituted with one halogen, and 3-6 membered heterocyclyl;

$R_3$ is ($C_1$-$C_4$) alkyl;

$R_4$ is selected from ($C_1$-$C_4$) alkyl optionally substituted with halogen, —$OR_6$, halogen, and 3-6 membered heterocyclyl;

$R_5$ is aryl substituted with one halogen;

$R_6$ is selected from aryl, and ($C_1$-$C_4$) alkyl optionally substituted with halogen;

L is —NHC(O)—;

x is zero or one;

$Ar_1$ is a heteroaryl or bicyclic heteroaryl and is optionally substituted with one ($C_1$-$C_4$) alkyl;

$Ar_2$ is an aryl or heteroaryl, optionally substituted with 1-2 $R_7$;

$R_7$ is selected from: aryl, halogen, trifluoromethyl, and —$NHS(O)_2R_8$ $R_8$ is aryl optionally substituted with one $R_9$; and $R_9$ is halogen or aryl.

In some embodiments, $R_1$ is selected from ($C_1$-$C_4$) alkyl optionally substituted with 1-3 $R_2$, ($C_3$-$C_6$) cycloalkyl optionally substituted with one $R_3$, aryl optionally substituted with 1-2 $R_4$, heteroaryl substituted with one $R_5$, bicyclic heteroaryl substituted with one ($C_1$-$C_4$) alkyl, and

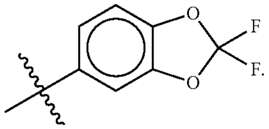

In some embodiments, $R_1$ is ($C_1$-$C_4$) alkyl optionally substituted with 1-3 $R_2$. In some embodiments, $R_1$ is $C_1$ alkyl substituted with 1 $R_2$. In some embodiments, $R_1$ is $C_1$ alkyl substituted with 2 $R_2$. In some embodiments, $R_1$ is $C_1$ alkyl substituted with 3 $R_2$. In some embodiments, $R_1$ is unsubstituted $C_1$ alkyl. In some embodiments, $R_1$ is $C_2$ alkyl substituted with 1 $R_2$. In some embodiments, $R_1$ is $C_2$ alkyl substituted with 2 $R_2$. In some embodiments, $R_1$ is $C_2$ alkyl substituted with 3 $R_2$. In some embodiments, $R_1$ is unsubstituted $C_2$ alkyl. In some embodiments, $R_1$ is methyl substituted with 1 $R_2$. In some embodiments, $R_1$ is methyl substituted with 2 $R_2$. In some embodiments, $R_1$ is methyl substituted with 3 $R_2$. In some embodiments, $R_1$ is unsubstituted methyl. In some embodiments, $R_1$ is ethyl substituted with 1 $R_2$. In some embodiments, $R_1$ is ethyl substituted with 2 $R_2$. In some embodiments, $R_1$ is ethyl substituted with 3 $R_2$. In some embodiments, $R_1$ is unsubstituted ethyl.

In some embodiments, $R_1$ is ($C_3$-$C_6$) cycloalkyl optionally substituted with one $R_3$. In some embodiments, $R_1$ is a $C_6$ cycloalkyl optionally substituted with one $R_3$. In some embodiments, $R_1$ is a $C_6$ cycloalkyl substituted with 1 $R_3$. In some embodiments, $R_1$ is cyclohexyl optionally substituted with 1 $R_3$. In some embodiments, $R_1$ is cyclohexyl substituted with 1 $R_3$.

In some embodiments, $R_1$ is aryl optionally substituted with 1-2 $R_4$. In some embodiments, $R_1$ is aryl substituted with 1 $R_4$. In some embodiments, $R_1$ is aryl substituted with 2 $R_4$. In some embodiments, $R_1$ is unsubstituted aryl. In some embodiments, $R_1$ is phenyl substituted with 1 $R_4$. In some embodiments, $R_1$ is phenyl substituted with 2 $R_4$. In some embodiments, $R_1$ is unsubstituted phenyl. In some embodiments, $R_1$ is indanyl substituted with 1 $R_4$. In some embodiments, $R_1$ is unsubstituted indanyl. In some embodiments, $R_1$ is unsubstituted tetrahydronaphthenyl.

In some embodiments, $R_1$ is heteroaryl substituted with one $R_5$. In some embodiments, $R_1$ is pyrazolyl substituted with 1 $R_5$.

In some embodiments, $R_1$ is bicyclic heteroaryl substituted with 1 ($C_1$-$C_4$) alkyl. In some embodiments, $R_1$ is bicyclic heteroaryl substituted with 1 $C_3$ alkyl. In some embodiments, $R_1$ is bicyclic heteroaryl substituted with 1 isopropyl. In some embodiments, $R_1$ is indazolyl substituted with 1 ($C_1$-$C_4$) alkyl. In some embodiments, $R_1$ is indazolyl substituted with 1 $C_3$ alkyl. In some embodiments, $R_1$ is indazolyl substituted with 1 isopropyl.

In some embodiments, $R_1$ is

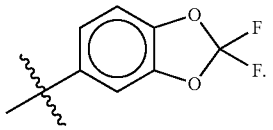

In some embodiments, $R_2$ is selected from ($C_1$-$C_4$) alkyl, ($C_3$-$C_6$) cycloalkyl, ($C_6$-$C_{12}$) spirocycloalkyl, aryl optionally substituted with one halogen or —$OR_6$, and 3-6 membered heterocyclyl.

In some embodiments, $R_2$ is ($C_1$-$C_4$) alkyl. In some embodiments, $R_2$ is $C_1$ alkyl. In some embodiments, $R_2$ is methyl.

In some embodiments, $R_2$ is ($C_3$-$C_6$) cycloalkyl.

In some embodiments, $R_2$ is ($C_6$-$C_{12}$) spirocycloalkyl. In some embodiments, $R_2$ is $C_8$ spirocycloalkyl. In some embodiments, $R_2$ is spirooctane. In some embodiments, $R_2$ is spiro[5.2]octane.

In some embodiments, $R_2$ is aryl optionally substituted with one halogen or —$OR_6$. In some embodiments, $R_2$ is unsubstituted aryl. In some embodiments, $R_2$ is unsubstituted phenyl. In some embodiments, $R_2$ is aryl substituted with 1 halogen. In some embodiments, $R_2$ is aryl substituted with 1 Cl. In some embodiments, $R_2$ is phenyl substituted with 1 halogen. In some embodiments, $R_2$ is phenyl substituted with 1 Cl. In some embodiments, $R_2$ is aryl substituted with 1 —$OR_6$. In some embodiments, $R_2$ is phenyl substituted with 1 —$OR_6$.

In some embodiments, $R_2$ is 3-6 membered heterocyclyl. In some embodiments, $R_2$ is a 5-member heterocyclyl. In some embodiments $R_2$ is pyrrolidinyl.

In some embodiments, $R_2$ is selected from the group consisting of: methyl, cyclopropyl fused to cyclohexyl, pyrrolidinyl, and phenyl optionally substituted with one —Cl.

In some embodiments, $R_3$ is ($C_1$-$C_4$) alkyl. In some embodiments, $R_3$ is $C_4$ alkyl. In some embodiments, $R_3$ is tert-butyl.

In some embodiments, $R_4$ is selected from ($C_1$-$C_4$) alkyl optionally substituted with halogen, —$OR_6$, halogen, and 3-6 membered heterocyclyl.

In some embodiments, $R_4$ is ($C_1$-$C_4$) alkyl optionally substituted with halogen. In some embodiments, $R_4$ is $C_1$ alkyl optionally substituted with halogen. In some embodiments, $R_4$ is unsubstituted $C_1$ alkyl. In some embodiments, $R_4$ is $C_1$ alkyl substituted with halogen. In some embodiments, $R_4$ is $C_1$ alkyl substituted with 1 halogen. In some embodiments, $R_4$ is $C_1$ alkyl substituted with 2 halogen. In some embodiments, $R_4$ is $C_1$ alkyl substituted with 3 halogen. In some embodiments, $R_4$ is $C_1$ alkyl substituted with 2 F. In some embodiments, $R_4$ is $C_1$ alkyl substituted with 3 F. In some embodiments, $R_4$ is methyl optionally substituted with halogen. In some embodiments, $R_4$ is unsubstituted methyl. In some embodiments, $R_4$ is methyl substituted with halogen. In some embodiments, $R_4$ is methyl substituted with 1 halogen. In some embodiments, $R_4$ is methyl substituted with 2 halogen. In some embodiments, $R_4$ is methyl substituted with 3 halogen. In some embodiments, $R_4$ is methyl substituted with 2 F. In some embodiments, $R_2$ is difluoromethyl. In some embodiments, $R_4$ is $C_1$ alkyl substituted with 3 F. In some embodiments, $R_4$ is trifluoromethyl. In some embodiments, $R_4$ is $C_3$ alkyl optionally substituted with halogen. In some embodiments, $R_4$ is unsubstituted $C_3$ alkyl. In some embodiments, $R_4$ is isopropyl optionally substituted with halogen. In some embodiments, $R_4$ is unsubstituted isopropyl.

In some embodiments, $R_4$ is —$OR_6$.

In some embodiments, $R_4$ is halogen. In some embodiments, $R_4$ is a halogen selected from F, Cl, Br, and I. In some embodiments, $R_4$ is a halogen selected from Cl, Br, and I. In some embodiments, $R_4$ is a halogen selected from F, Cl, and Br. In some embodiments, $R_4$ is a halogen selected from F, Cl, and I. In some embodiments, $R_4$ is F. In some embodiments, $R_4$ is Cl. In some embodiments, $R_4$ is Br. In some embodiments, $R_4$ is I.

In some embodiments, $R_4$ is 3-6 heterocyclyl. In some embodiments, $R_4$ is 5-member heterocyclyl. In some embodiments, $R_4$ is pyrrolidinyl.

In some embodiments, $R_4$ is selected from the group consisting of: methyl, isopropyl, trifluoromethyl, —Cl, and pyrrolidinyl.

In some embodiments, $R_5$ aryl substituted with one halogen. In some embodiments, $R_5$ is aryl substituted with one halogen selected from F, Cl, Br, and I. In some embodiments, $R_5$ is aryl substituted with one F. In some embodiments, $R_5$ is aryl substituted with one $C_1$. In some embodiments, $R_5$ is aryl substituted with one Br. In some embodiments, $R_5$ is aryl substituted with one I. In some embodiments, $R_5$ phenyl substituted with one halogen. In some embodiments, $R_5$ is phenyl substituted with one halogen selected from F, Cl, Br, and I. In some embodiments, $R_5$ is phenyl substituted with one F. In some embodiments, $R_5$ is phenyl substituted with one $C_1$. In some embodiments, $R_5$ is phenyl substituted with one Br. In some embodiments, $R_5$ is phenyl substituted with one I.

In some embodiments, $R_6$ selected from aryl, and ($C_1$-$C_4$) alkyl optionally substituted with halogen.

In some embodiments, $R_6$ is aryl. In some embodiments, $R_6$ is phenyl.

In some embodiments, $R_6$ is ($C_1$-$C_4$) alkyl optionally substituted with halogen. In some embodiments, $R_6$ is $C_1$ alkyl optionally substituted with halogen. In some embodiments, $R_6$ is unsubstituted $C_1$ alkyl. In some embodiments, $R_{46}$ is $C_1$ alkyl substituted with halogen. In some embodiments, $R_6$ is $C_1$ alkyl substituted with 1 halogen. In some embodiments, $R_6$ is $C_1$ alkyl substituted with 2 halogen. In some embodiments, $R_6$ is $C_1$ alkyl substituted with 3 halogen. In some embodiments, $R_6$ is $C_1$ alkyl substituted with 2 F. In some embodiments, $R_6$ is $C_1$ alkyl substituted with 3 F. In some embodiments, $R_6$ is methyl optionally substituted with halogen. In some embodiments, $R_6$ is unsubstituted methyl. In some embodiments, $R_6$ is methyl substituted with halogen. In some embodiments, $R_6$ is methyl substituted with 1 halogen. In some embodiments, $R_6$ is methyl substituted with 2 halogen. In some embodiments, $R_6$ is methyl substituted with 3 halogen. In some embodiments, $R_6$ is methyl substituted with 2 F. In some embodiments, $R_6$ is difluoromethyl. In some embodiments, $R_6$ is $C_1$ alkyl substituted with 3 F. In some embodiments, $R_6$ is trifluoromethyl. In some embodiments, $R_6$ is $C_3$ alkyl optionally substituted with halogen. In some embodiments, $R_6$ is unsubstituted $C_3$ alkyl. In some embodiments, $R_6$ is isopropyl optionally substituted with halogen. In some embodiments, $R_6$ is unsubstituted isopropyl.

In some embodiments, $R_6$ is selected from the group consisting of: phenyl, isopropyl, difluoromethyl, and trifluoromethyl.

In some embodiments, x is zero. In some embodiments, x is one.

In some embodiments, $Ar_1$ is a heteroaryl or bicyclic heteroaryl and is optionally substituted with one ($C_1$-$C_4$) alkyl. In some embodiments, $Ar_1$ is a heteroaryl optionally substituted with one ($C_1$-$C_4$) alkyl. In some embodiments, $Ar_1$ is a heteroaryl substituted with 1 ($C_1$-$C_4$) alkyl. In some embodiments, $Ar_1$ is isothiazolyl substituted with 1 $C_1$ alkyl. In some embodiments, $Ar_1$ is isothiazolyl substituted with 1 methyl. In some embodiments, $Ar_1$ is an unsubstituted heteroaryl. In some embodiments, $Ar_1$ is unsubstituted 1,2,3-thiadiazolyl. In some embodiments, $Ar_1$ is 1,2,4-thiadiazolyl. In some embodiments, $Ar_1$ is unsubstituted thiazolyl. In some embodiments, $Ar_1$ is a bicyclic heteroaryl optionally substituted with one ($C_1$-$C_4$) alkyl. In some embodiments, $Ar_1$ is a bicyclic heteroaryl substituted with one ($C_1$-$C_4$) alkyl. In some embodiments, $Ar_1$ is an unsubstituted bicyclic heteroaryl. In some embodiments, $Ar_1$ is unsubstituted 6,7-dihydro-4H-thieno[3.2-c]pyran.

In some embodiments, $Ar_2$ is an aryl or heteroaryl, optionally substituted with 1-2 $R_7$. In some embodiments, $Ar_2$ is an unsubstituted aryl. In some embodiments, $Ar_2$ is an aryl substituted with 1 $R_7$. In some embodiments, $Ar_2$ is phenyl substituted with 1 $R_7$. In some embodiments, $Ar_2$ is an aryl substituted with 2 $R_7$. In some embodiments, $Ar_2$ is phenyl substituted with 2 $R_7$. In some embodiments, $Ar_2$ is an unsubstituted heteroaryl. In some embodiments, $Ar_2$ is a heteroaryl substituted with 1 $R_7$. In some embodiments, $Ar_2$ is a pyridinyl substituted with 1 $R_7$. In some embodiments, $Ar_2$ is 1,2,3-thiadiazolyl substituted with 1 $R_7$. In some embodiments, $Ar_2$ is a heteroaryl substituted with 2 $R_7$.

In some embodiments, $R_7$ is selected from aryl, halogen, trifluoromethyl and —$NHS(O)_2R_8$. In some embodiments, $R_7$ is aryl. In some embodiments, $R_7$ is phenyl. In some embodiments, $R_7$ is halogen. In some embodiments, $R_7$ is halogen selected from F, Cl, Br, I. In some embodiments, $R_7$ is F. In some embodiments, $R_7$ is Cl. In some embodiments, $R_7$ is Br. In some embodiments, $R_7$ is I. In some embodiments, $R_7$ is trifluoromethyl. In some embodiments, $R_7$ is —$NHSO(O)_2R_8$.

In some embodiments, $R_8$ is aryl optionally substituted with one $R_9$. In some embodiments, $R_8$ is unsubstituted aryl. In some embodiments, $R_8$ is aryl substituted with one $R_9$. In some embodiments, $R_8$ is phenyl optionally substituted with one $R_9$. In some embodiments, $R_8$ is unsubstituted phenyl. In some embodiments, $R_8$ is phenyl substituted with one $R_9$.

In some embodiments, $R_9$ is halogen or aryl. In some embodiments, $R_9$ is halogen. In some embodiments, $R_9$ is halogen selected from F, Cl, Br, and I. In some embodiments, $R_9$ is F. In some embodiments, $R_9$ is Cl. In some embodiments, $R_9$ is Br. In some embodiments, $R_9$ is I. In some embodiments, $R_9$ is aryl. In some embodiments, $R_9$ is phenyl.

In some embodiments, a compound of formula (I) is selected from a group consisting of the compounds recited in Table A.

In some embodiments, the disclosure relates to compounds of formula (I) that are further given by formula (II):

(II)

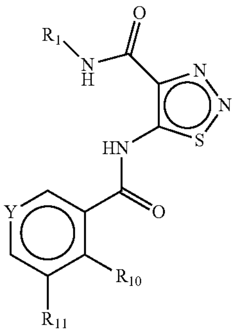

and pharmaceutically acceptable salts, hydrates, solvates, isomers, and tautomers thereof, wherein:

Y is N or CH;

$R_{10}$ is hydrogen or halogen; and $R_{11}$ is halogen or $(C_1\text{-}C_3)$ alkyl substituted with halogen.

In some embodiments, $R_{10}$ is hydrogen or halogen. In some embodiments, $R_{10}$ is hydrogen. In some embodiments, $R_{10}$ is halogen. In some embodiments, $R_{10}$ is a halogen selected from F, Cl, Br, and I. In some embodiments, $R_{10}$ is hydrogen or C. In some embodiments, $R_{10}$ is Cl.

In some embodiments, $R_{11}$ is halogen or $(C_1\text{-}C_3)$ alkyl substituted with halogen. In some embodiments, $R_{11}$ is a halogen selected from the group consisting of F, Cl, Br, and I. In some embodiments, $R_{11}$ is $(C_1\text{-}C_3)$ alkyl substituted with halogen. In some embodiments, $R_{11}$ is $(C_1\text{-}C_3)$ alkyl substituted with 1 halogen. In some embodiments, $R_{11}$ is $(C_1\text{-}C_3)$ alkyl substituted with 2 halogen. In some embodiments, $R_{11}$ is $(C_1\text{-}C_3)$ alkyl substituted with 3 halogen. In some embodiments, $R_{11}$ is $C_1$ alkyl substituted with halogen. In some embodiments, $R_{11}$ is $C_1$ alkyl substituted with 1 halogen. In some embodiments, $R_{11}$ is $C_1$ alkyl substituted with 2 halogen. In some embodiments, $R_{11}$ is $C_1$ alkyl substituted with 3 halogen. In some embodiments, $R_{11}$ is methyl substituted with halogen. In some embodiments, $R_{11}$ is methyl substituted with 1 halogen. In some embodiments, $R_{11}$ is methyl substituted with 2 halogen. In some embodiments, $R_{11}$ is methyl substituted with 3 halogen. In some embodiments, $R_{11}$ is Cl or trifluoromethyl. In some embodiments, $R_{11}$ is Cl. In some embodiments, $R_{11}$ is trifluoromethyl.

In some embodiments, a compound of formula (II) is selected from the group consisting of:

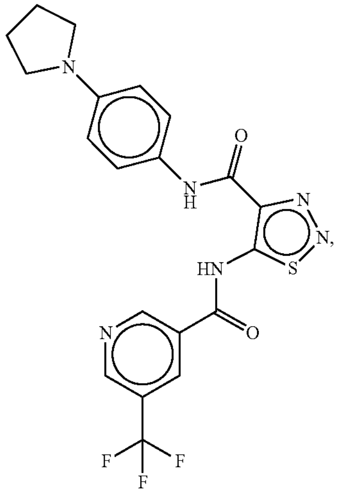

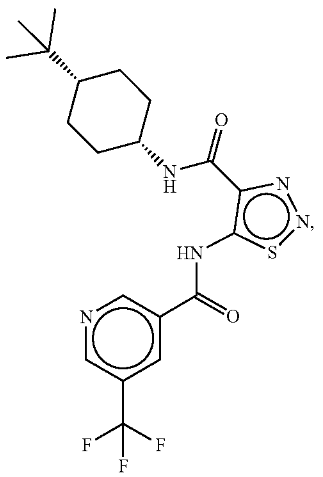

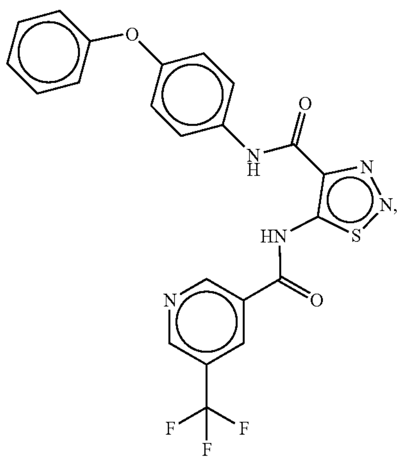

-continued
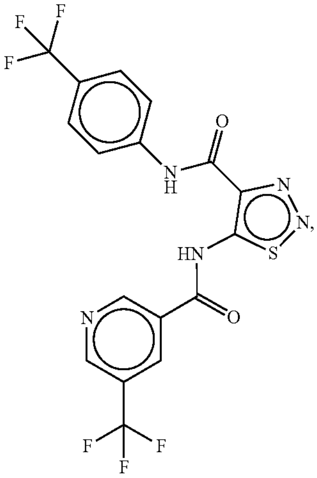
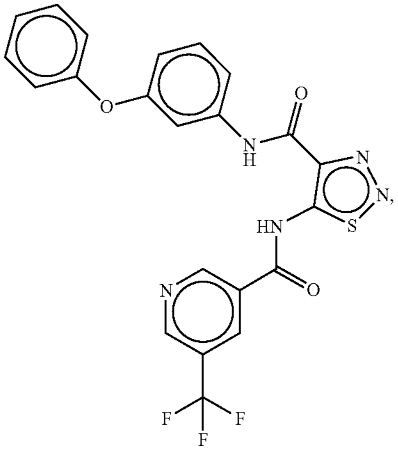
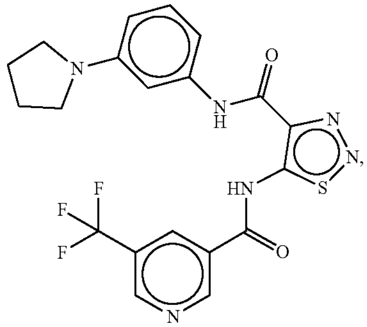
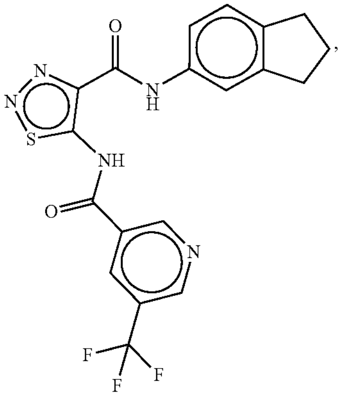
-continued
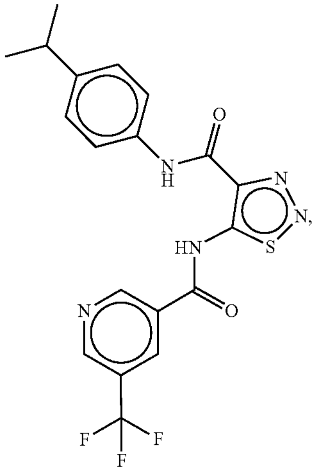
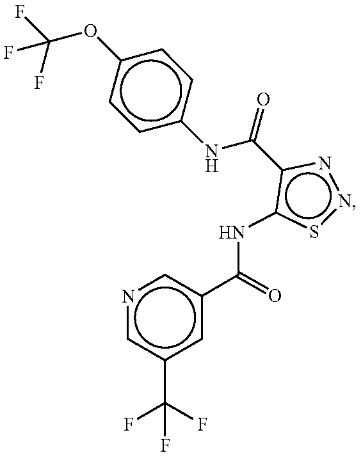
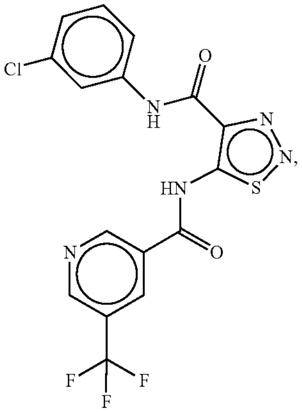

-continued
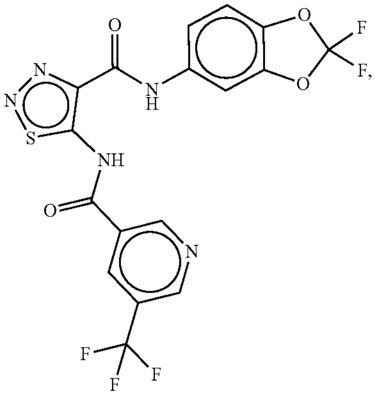
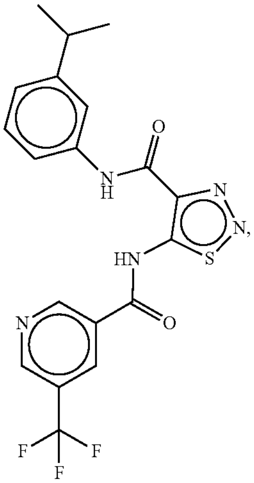
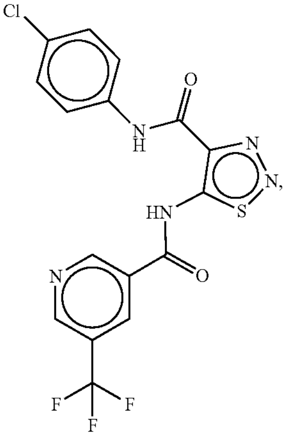
-continued
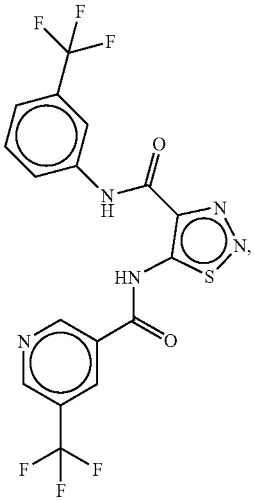
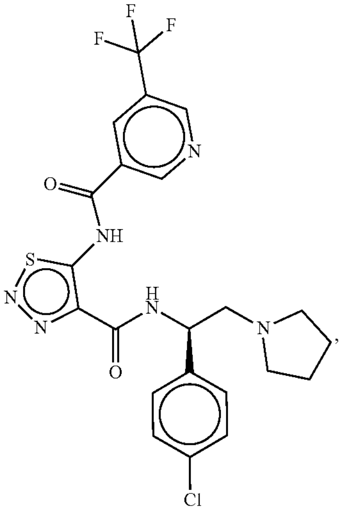
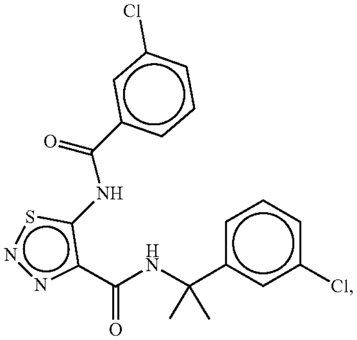
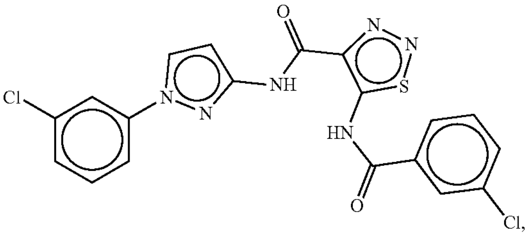

-continued
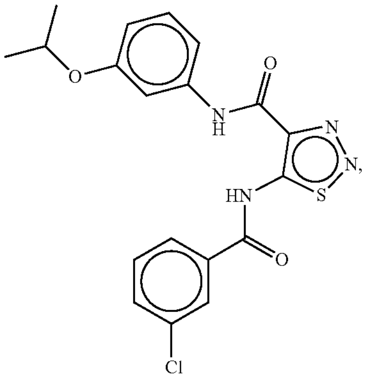
,
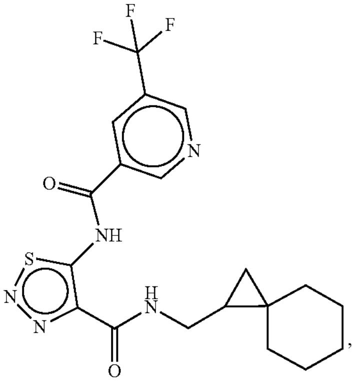
,
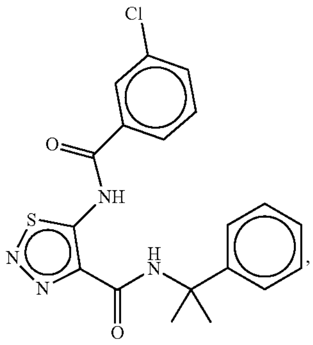
,
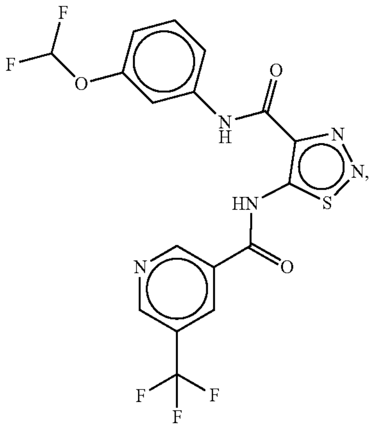
,
-continued
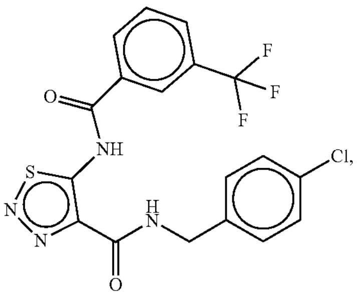
,
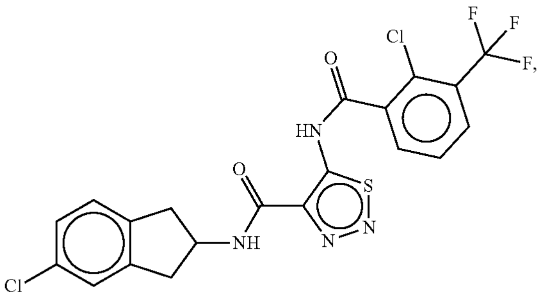
,
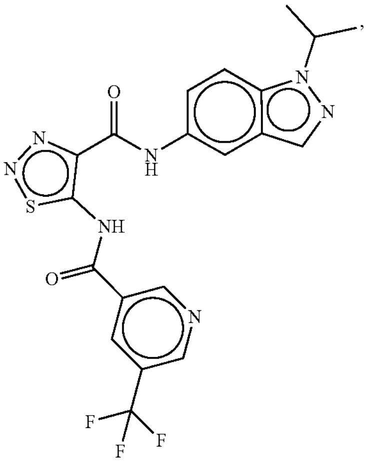
,
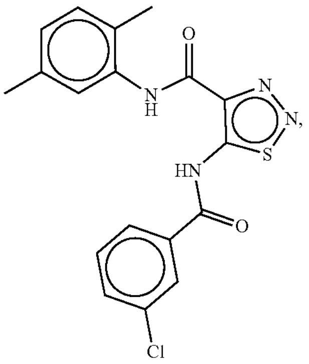
, -continued

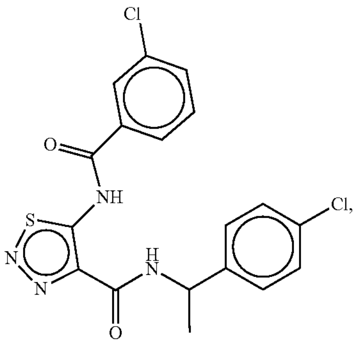

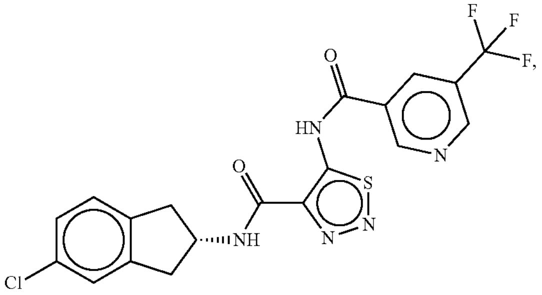

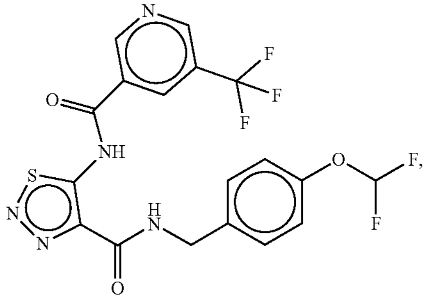

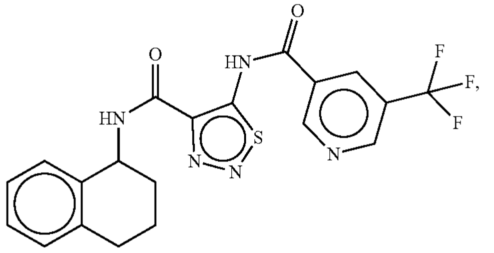

and

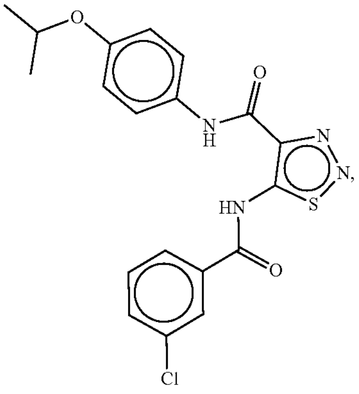

or a pharmaceutically acceptable salt or isomer thereof.

In some embodiments, the disclosure relates to compounds of formula (I) that are further given by formula (III):

(III)

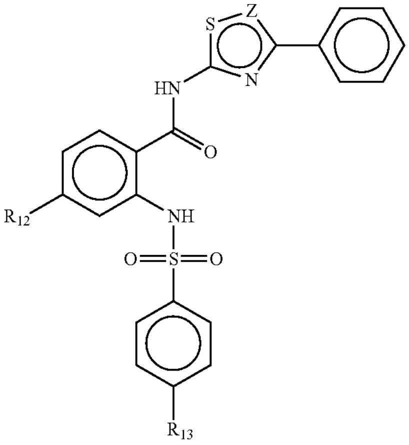

and pharmaceutically acceptable salts, hydrates, solvates, isomers, and tautomers thereof, wherein:

Z is N or CH;

$R_{12}$ is hydrogen or ($C_1$-$C_4$) alkyl substituted with one or more halogen atoms; and $R_{13}$ is aryl or halogen.

In some embodiments, $R_{12}$ is hydrogen or ($C_1$-$C_4$) alkyl substituted with one or more halogen atoms. In some embodiments, $R_{12}$ is ($C_1$-$C_4$) alkyl substituted with one or more halogen atoms. In some embodiments, $R_{12}$ is ($C_1$-$C_4$) alkyl substituted with 1 halogen. In some embodiments, $R_{12}$ is ($C_1$-$C_4$) alkyl substituted with 2 halogen. In some embodiments, $R_{12}$ is ($C_1$-$C_4$) alkyl substituted with 3 halogen. In some embodiments, $R_{12}$ is $C_1$ alkyl substituted with halogen. In some embodiments, $R_{12}$ is $C_1$ alkyl substituted with 1 halogen. In some embodiments, $R_{12}$ is $C_1$ alkyl substituted with 2 halogen. In some embodiments, $R_{12}$ is $C_1$ alkyl substituted with 3 halogen. In some embodiments, $R_{12}$ is methyl substituted with halogen. In some embodiments, $R_{12}$ is methyl substituted with 1 halogen. In some embodiments, $R_{12}$ is methyl substituted with 2 halogen. In some embodiments, $R_{12}$ is methyl substituted with 3 halogen. In some embodiments, $R_{12}$ is hydrogen or trifluoromethyl. In some embodiments, $R_{12}$ is hydrogen. In some embodiments, $R_{12}$ is trifluoromethyl.

In some embodiments, $R_{13}$ is aryl or halogen. In some embodiments $R_{13}$ is aryl. In some embodiments $R_{13}$ is halogen. In some embodiments, $R_{13}$ is halogen selected from F, Cl, Br, and I. In some embodiments, $R_{13}$ is phenyl or Cl. In some embodiments, $R_{13}$ is phenyl. In some embodiments, $R_{13}$ is Cl.

In some embodiments, a compound of formula (III) is selected from the group consisting of:

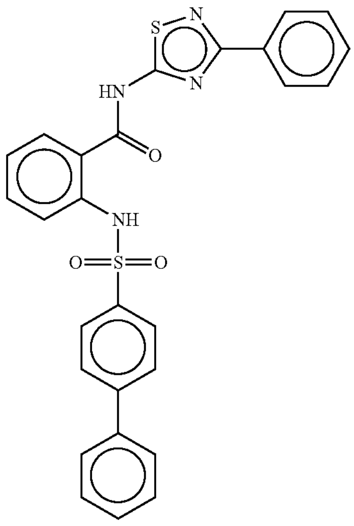

and

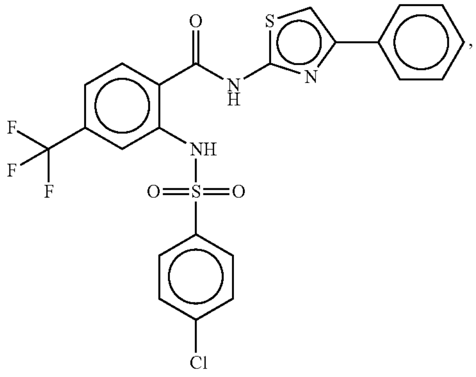

, or a pharmaceutically acceptable salt thereof.

In some embodiments, the disclosure relates to a compound of formula (I), which is further given by formula (IV):

(IV)

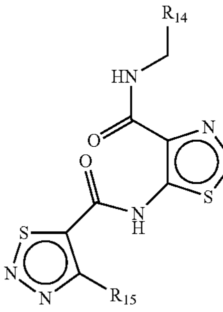

or a pharmaceutically acceptable salt, hydrate, solvate, isomer, or tautomer thereof, wherein:

$R_{14}$ is aryl substituted with halogen; and $R_{15}$ is aryl.

In some embodiments, $R_{14}$ is aryl substituted with halogen. In some embodiments, $R_{14}$ is aryl substituted with 1 halogen. In some embodiments, $R_{14}$ is aryl substituted with 1 halogen selected from the group consisting of F, Cl, Br, and I. In some embodiments, $R_{14}$ is aryl substituted with 1 Cl. In some embodiments, $R_{14}$ is phenyl substituted with halogen. In some embodiments, $R_{14}$ is phenyl substituted with 1 halogen. In some embodiments, $R_{14}$ is phenyl substituted with 1 halogen selected from the group consisting of F, Cl, Br, and I. In some embodiments, $R_{10}$ is phenyl substituted with 1 Cl.

In some embodiments, $R_{15}$ is aryl. In some embodiments, $R_{15}$ is phenyl.

In some embodiments, the compound of formula (IV) is:

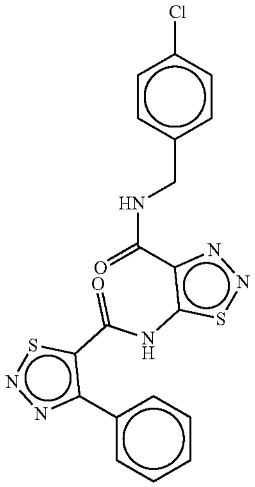

or a pharmaceutically acceptable salt thereof.

In some embodiments, the disclosure relates to a compound of formula (I), which is further given by formula (V):

(V)

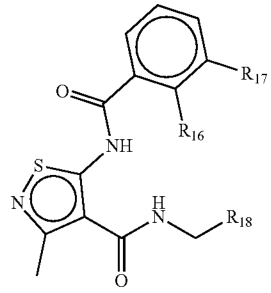

or a pharmaceutically acceptable salt, hydrate, solvate, isomer, or tautomer thereof, wherein:

$R_{16}$ is halogen; $R_{17}$ is $(C_1-C_4)$ alkyl substituted with halogen; and $R_{18}$ is aryl substituted with halogen.

In some embodiments, $R_{16}$ is halogen. In some embodiments, $R_{16}$ is halogen selected from the group consisting of F, Cl, Br, and I. In some embodiments, $R_{16}$ is Cl.

In some embodiments, $R_{17}$ is $(C_1-C_4)$ alkyl substituted with halogen. In some embodiments, $R_{17}$ is $C_1$ alkyl substituted with halogen. In some embodiments, $R_{17}$ is $C_1$ alkyl substituted with 3 halogen. In some embodiments, $R_{17}$ is $C_1$ alkyl substituted with 3 halogen selected from the group consisting of F, Cl, Br, and I. In some embodiments, $R_{17}$ is $C_1$ alkyl substituted with 3 F. In some embodiments, $R_{17}$ is methyl substituted with halogen. In some embodiments, $R_{17}$ is methyl substituted with 3 halogen. In some embodiments, $R_{17}$ is methyl substituted with 3 halogen selected from the group consisting of F, Cl, Br, and I. In some embodiments, $R_{17}$ is methyl substituted with 3 F. In some embodiments, $R_{17}$ is trifluoromethyl.

In some embodiments, $R_{18}$ is aryl substituted with halogen. In some embodiments, $R_{18}$ is aryl substituted with 1 halogen. In some embodiments, $R_{18}$ is aryl substituted with 1 halogen selected from the group consisting of F, Cl, Br, and I. In some embodiments, $R_{18}$ is aryl substituted with 1 Cl. In some embodiments, $R_{18}$ is phenyl substituted with halogen. In some embodiments, $R_{18}$ is phenyl substituted with 1 halogen. In some embodiments, $R_{18}$ is phenyl substituted with 1 halogen selected from the group consisting of F, Cl, Br, and I. In some embodiments, $R_{18}$ is phenyl substituted with 1 Cl.

In some embodiments, the compound of formula (V) is:

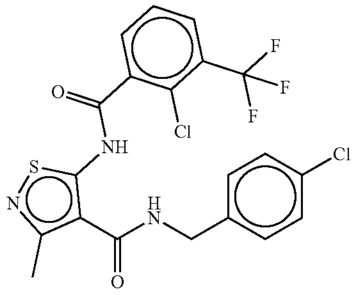

or a pharmaceutically acceptable salt thereof.

In some embodiments, the disclosure relates to a compound of formula (I), which is further given by formula (VI):

(VI)

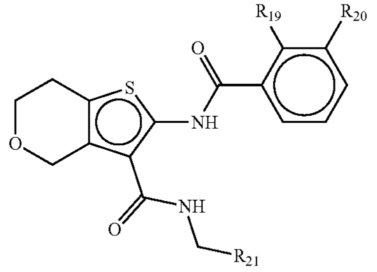

or a pharmaceutically acceptable salt, hydrate, solvate, isomer, or tautomer thereof, wherein:

$R_{19}$ is halogen;

$R_{20}$ is ($C_1$-$C_4$) alkyl substituted with halogen; and $R_{21}$ is aryl substituted with halogen.

In some embodiments, $R_{19}$ is halogen. In some embodiments, $R_{19}$ is halogen selected from the group consisting of F, Cl, Br, and I. In some embodiments, $R_{19}$ is Cl.

In some embodiments, $R_{20}$ is ($C_1$-$C_4$) alkyl substituted with halogen. In some embodiments, $R_{20}$ is $C_1$ alkyl substituted with halogen. In some embodiments, $R_{20}$ is $C_1$ alkyl substituted with 3 halogen. In some embodiments, $R_{20}$ is $C_1$ alkyl substituted with 3 halogen selected from the group consisting of F, Cl, Br, and I. In some embodiments, $R_{20}$ is $C_1$ alkyl substituted with 3 F. In some embodiments, $R_{20}$ is methyl substituted with halogen. In some embodiments, $R_{20}$ is methyl substituted with 3 halogen. In some embodiments, $R_{20}$ is methyl substituted with 3 halogen selected from the group consisting of F, Cl, Br, and I. In some embodiments, $R_{20}$ is methyl substituted with 3 F. In some embodiments, $R_{20}$ is trifluoromethyl.

In some embodiments, $R_{21}$ is aryl substituted with halogen. In some embodiments, $R_{21}$ is aryl substituted with 1 halogen. In some embodiments, $R_{21}$ is aryl substituted with 1 halogen selected from the group consisting of F, Cl, Br, and I. In some embodiments, $R_{21}$ is aryl substituted with 1 Cl. In some embodiments, $R_{21}$ is phenyl substituted with halogen. In some embodiments, $R_{21}$ is phenyl substituted with 1 halogen. In some embodiments, $R_{21}$ is phenyl substituted with 1 halogen selected from the group consisting of F, Cl, Br, and I. In some embodiments, $R_{21}$ is phenyl substituted with 1 Cl.

In some embodiments, the compound of formula (VI) is:

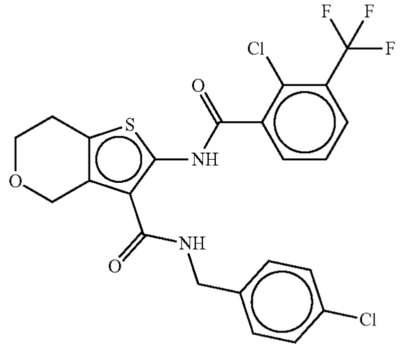

or a pharmaceutically acceptable salt thereof.

A compound of formula (I) is not:

2-((4-fluorophenyl)sulfonamido)-N-(4-phenylthiazol-2-yl) benzamide;

2-[[(4-chlorophenyl)sulfonyl]amino]-N-[4-(2,5-dimethoxyphenyl)-2-thiazolyl]-benzamide;

N-[4-(1,3-benzodioxol-5-yl)-2-thiazolyl]-2-[[(4-chlorophenyl)sulfonyl]amino]-benzamide;

N-[4-(3,4-dimethoxyphenyl)-2-thiazolyl]-2-[[(4-fluorophenyl)sulfonyl]amino]-benzamide;

N-[4-(2,4-dimethoxyphenyl)-2-thiazolyl]-2-[[(4-fluorophenyl)sulfonyl]amino]-benzamide;

2-[[(4-chlorophenyl)sulfonyl]amino]-N-[4-(2,4-dimethoxyphenyl)-2-thiazolyl]-benzamide;

2-[[(4-chlorophenyl)sulfonyl]amino]-N-[4-(2,3-dihydro-1,4-benzodioxin-6-yl)-2-thiazolyl]-benzamide;

N-[4-(2,5-dimethoxyphenyl)-2-thiazolyl]-2-[[(4-fluorophenyl)sulfonyl]amino]-benzamide;

2-[[(4-chlorophenyl)sulfonyl]amino]-N-[4-(3,4-dimethoxyphenyl)-2-thiazolyl]-benzamide;

N-[4-(2,5-dimethoxyphenyl)-2-thiazolyl]-2-[(phenylsulfonyl)amino]-benzamide;

N-[4-(2,3-dihydro-1,4-benzodioxin-6-yl)-2-thiazolyl]-2-[[(4-fluorophenyl)sulfonyl]amino]-benzamide;

2-[[(4-fluorophenyl)sulfonyl]amino]-N-[4-(4-fluorophenyl)-2-thiazolyl]-benzamide;

N-[4-(2,4-dimethoxyphenyl)-2-thiazolyl]-2-[(phenylsulfonyl)amino]-benzamide;

2-[[(4-fluorophenyl)sulfonyl]amino]-N-(3-phenyl-1,2,4-thiadiazol-5-yl)-benzamide;

N-[4-(4-ethoxyphenyl)-2-thiazolyl]-2-[(phenylsulfonyl) amino]-benzamide;

2-[[(4-fluorophenyl)sulfonyl]amino]-N-[4-(4-methoxyphenyl)-2-thiazolyl]-benzamide;

N-[4-(3,4-dimethoxyphenyl)-2-thiazolyl]-2-[(phenylsulfonyl)amino]-benzamide;

N-[4-(4-methoxyphenyl)-2-thiazolyl]-2-[(phenylsulfonyl) amino]-benzamide;

N-[4-(4-ethoxyphenyl)-2-thiazolyl]-2-[[(4-fluorophenyl) sulfonyl]amino]-benzamide;

N-[4-(1,3-benzodioxol-5-yl)-2-thiazolyl]-2-[[(4-fluorophenyl)sulfonyl]amino]-benzamide;

N-[4-(4-methoxy-3-methylphenyl)-2-thiazolyl]-2-[(phenyl sulfonyl)amino]-benzamide;

N-[4-(1,3-benzodioxol-5-yl)-2-thiazolyl]-2-[(phenylsulfonyl)amino]-benzamide;

N-[4-(2,3-dihydro-1,4-benzodioxin-6-yl)-2-thiazolyl]-2-[(phenylsulfonyl)amino]-benzamide;

2-[[(4-fluorophenyl)sulfonyl]amino]-N-[4-(4-methoxy-3-methylphenyl)-2-thiazolyl]-benzamide;

N-[4-(4-fluorophenyl)-2-thiazolyl]-2-[(phenylsulfonyl)amino]-benzamide;

N-[4-(4-methylphenyl)-2-thiazolyl]-2-[(phenylsulfonyl)amino]-benzamide;

2-[[(4-fluorophenyl)sulfonyl]amino]-N-[4-(4-methylphenyl)-2-thiazolyl]-benzamide;

2-[[(4-fluorophenyl)sulfonyl]amino]-N-[4-[4-(1-methylethyl)phenyl]-2-thiazolyl]-benzamide; or 2-[[(4-chlorophenyl)sulfonyl]amino]-N-[4-(2-naphthalenyl)-2-thiazolyl]-benzamide.

Non-limiting, specific embodiments of the USP36 Inhibitor Compounds are shown in Table A below.

Methods of Preparing the Compounds of the Disclosure

The compounds of the present disclosure may be made by a variety of methods, including standard chemistry. Suitable synthetic routes are depicted in the examples given below.

The compounds of the present disclosure, i.e., compounds of formulas (I)-(VI) or a pharmaceutically acceptable salt thereof, may be prepared by methods known in the art of organic synthesis as set forth in part by the synthetic schemes depicted in the examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of formulas (I)-(VI).

Those skilled in the art will recognize stereocenters exist in the compounds of formulas (I)-(VI). Accordingly, the present disclosure includes both possible stereoisomers (unless otherwise indicated and/or specified in the synthesis) and includes not only racemic compounds but the individual enantiomers and/or diastereomers as well. Unless otherwise indicated, when a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Methods of Using the Compounds of the Disclosure

One aspect of the present disclosure relates to a compound of any one of formulas (I)-(VI) for use in medicine. Another aspect of the present disclosure relates to a method of modulating USP36, comprising administering to a patient in need thereof a therapeutically effective amount of a compound of any one of formulas (I)-(VI). Another aspect of the present disclosure relates to a method of inhibiting one or more of USP36, comprising administering to a patient in need thereof a therapeutically effective amount of a compound of any one of formulas (I)-(VI). In another aspect, the present disclosure relates to a method of inhibiting USP36, comprising administering to a patient in need thereof a therapeutically effective amount of a pharmaceutical composition comprising a compound of any one of formulas (I)-(VI).

USP36 Inhibitor Compounds are useful in the development of pharmaceutical compositions suitable for treatment of certain forms of cancer including, but not limited to, pancreatic cancer, colorectal cancer, lung cancer, brain cancer, ovarian cancer, or prostate cancer. USP36 Inhibitor Compounds are useful for treating disease states that are responsive to the inhibition of USP36. This disclosure relates to the treatment of certain forms of cancer. Inhibition of USP36 will selectively induce cancer cell cycle arrest and apoptosis by decreasing ribosomal biogenesis and transcription, disrupting downstream protein synthesis, and negatively impacting nucleolar morphology. Based on the relationship between USP36, MYC, and ribosome production, upregulation of MYC-induced nucleolar stress provides a marker for differing levels of nucleolar stress and consequent vulnerability to disrupted ribosomal biogenesis. As such, it has the potential to provide a mechanism for identifying cancer cells types likely to be the most susceptible to USP36 inhibition.

The disclosure also includes pharmaceutical compositions comprising an effective amount of a disclosed compound of any one of formulas (I)-(VI) and a pharmaceutically acceptable carrier.

The disclosure also includes pharmaceutical compositions comprising one or more compounds as described herein, or a pharmaceutically acceptable salt thereof, and a pharmaceutically acceptable carrier. In some embodiments, pharmaceutical compositions reported herein can be provided in a unit dosage form (e.g., capsule, tablet or the like). In some embodiments, pharmaceutical compositions reported herein can be provided in an oral dosage form. In some embodiments, an oral dosage form of a compound of any one of formulas (I)-(VI) can be a capsule. In some embodiments, an oral dosage form of a compound of any one of formulas (I)-(VI) is a tablet. In some embodiments, an oral dosage form comprises one or more fillers, disintigrants, lubricants, glidants, anti-adherents and/or anti-statics. In some embodiments, an oral dosage form is prepared via dry blending. In some embodiments, an oral dosage form is a tablet and is prepared via dry granulation.

Compositions in accordance with the present invention may be employed for administration in any appropriate manner, e.g., oral or buccal administration. When orally administered, the compound of formula I may be prepared as a mixture with excipients suitable for the manufacture of oral dosage forms such as tablets, in a solution or suspension, in hard or soft encapsulated form including gelatin encapsulated form, sachet, or lozenge. Suspensions for oral administration may be prepared according to any method known to those skilled in the art. For example, suspensions may be oily suspensions in which a compound of any one of formulas (I)-(VI) is suspended in a liquid suspension comprising, for example, vegetable oils such as olive oil, sesame oil, or coconut oil. The liquid suspension may also contain mineral oil.

Compositions may also be administered topically, e.g., for application to the skin, for example in the form of a cream, paste, lotion, gel, ointment, poultice, cataplasm, plaster, dermal patch or the like, or for ophthalmic application, for example in the form of an eye drop, -lotion or -gel formulation.

Compositions may also be administered parenterally, e.g., intravenous. Intravenous forms include, but are not limited to, bolus and drip injections. In some embodiments, the intravenous dosage forms are sterile or capable of being sterilized prior to administration to a subject since they typically bypass the subject's natural defenses against contaminants. Examples of intravenous dosage forms include, but are not limited to, Water for Injection USP; aqueous vehicles including, but not limited to, Sodium Chloride Injection, Ringer's Injection, Dextrose Injection, Dextrose and Sodium Chloride Injection, and Lactated Ringer's Injection; water-miscible vehicles including, but not limited to, ethyl alcohol, polyethylene glycol and polypropylene glycol; and non-aqueous vehicles including, but not limited to, corn oil, cottonseed oil, peanut oil, sesame oil, ethyl oleate, isopropyl myristate and benzyl benzoate.

Readily flowable forms, for example solutions, emulsions and suspensions, may also be employed e.g., for intralesional injection, or may be administered rectally, e.g., as an enema or suppository, or intranasal administration, e.g., as a nasal spray or aerosol. Macrocrystalline powders may be formulated for inhalation, e.g., delivery to the nose, sinus, throat or lungs. Transdermal compositions/devices and pessaries may also be employed for delivery of the compounds of the invention. The compositions may additionally contain agents that enhance the delivery of the compounds having Formula I (or other active agents), e.g., liposomes, polymers or co-polymers (e.g., branched chain polymers).

The pharmaceutical compositions of the present invention may further comprise one or more additives. Additives that are well known in the art include, e.g., detackifiers, anti-foaming agents, buffering agents, antioxidants (e.g., ascorbic acid, ascorbyl palmitate, sodium ascorbate, butylated hydroxyanisole (BHA), butylated hydroxytoluene (BHT), propyl gallate, malic acid, fumaric acid, potassium metabisulfite, sodium bisulfite, sodium metabisulfite, and tocopherols, e.g., α-tocopherol (vitamin E)), preservatives, chelating agents, viscomodulators, tonicifiers, flavorants, colorants, odorants, opacifiers, suspending agents, binders, fillers, plasticizers, lubricants, and mixtures thereof. The amounts of such additives can be readily determined by one skilled in the art, according to the particular properties desired, and can be formulated such that compounds having Formula I are stable, e.g., not reduced by antioxidant additives.

The additive may also comprise a thickening agent. Suitable thickening agents may be of those known and employed in the art, including, e.g., pharmaceutically acceptable polymeric materials and inorganic thickening agents. Exemplary thickening agents for use in the present pharmaceutical compositions include polyacrylate and polyacrylate co-polymer resins, for example poly-acrylic acid and poly-acrylic acid/methacrylic acid resins; celluloses and cellulose derivatives including: alkyl celluloses, e.g., methyl-, ethyl- and propyl-celluloses; hydroxyalkyl-celluloses, e.g., hydroxypropyl-celluloses and hydroxypropylalkyl-celluloses such as hydroxypropyl-methyl-celluloses; acylated celluloses, e.g., cellulose-acetates, cellulose-acetatephthallates, cellulose-acetatesuccinates and hydroxypropyl ethyl-cellulose phthallates; and salts thereof such as sodium-carboxymethyl-celluloses; polyvinylpyrrolidones, including for example poly-N-vinylpyrrolidones and vinylpyrrolidone co-polymers such as vinylpyrrolidone-vinylacetate co-polymers; polyvinyl resins, e.g., including polyvinylacetates and alcohols, as well as other polymeric materials including gum traganth, gum arabicum, alginates, e.g., alginic acid, and salts thereof, e.g., sodium alginates; and inorganic thickening agents such as atapulgite, bentonite and silicates including hydrophilic silicon dioxide products, e.g., alkylated (for example methylated) silica gels, in particular colloidal silicon dioxide products.

Such thickening agents as described above may be included, e.g., to provide a sustained release effect. However, where oral administration is intended, the use of thickening agents may not be required. Use of thickening agents is, on the other hand, indicated, e.g., where topical application is foreseen.

Although the dosage of a compound of any one of formulas (I)-(VI) will vary according to the activity and/or toxicity of the particular compound, the condition being treated, and the physical form of the pharmaceutical composition being employed for administration, it may be stated by way of guidance that a dosage selected in the range from 1 to 2000 mg/kg of body weight per day will often be suitable. Those of ordinary skill in the art are familiar with methods for determining the appropriate dosage.

EXAMPLES

Materials and Instrumentation

All solvents used were commercially available and were used without further purification. Reactions were typically run using anhydrous solvents under an inert atmosphere of nitrogen. Proton NMR spectra was recorded using a Bruker 400 MHz NMR Spectrometer. The deuterated solvent (DMSO-d6) contained typically 0.03% to 0.05% v/v tetramethylsilane, which was used as the reference signal (set at δ 0.00 for 1H). LCMS analyses were performed on a SHIMADZU LCMS consisting of an UFLC 20-AD and LCMS 2020 MS detector. The column was used was a Shim-pack XR-ODS, 2.2 μm, 3.0×50 mm. The instrument using reverse-phase conditions (acetonitrile/water, containing 10 mM ammonium bicarbonate).

Definitions used in the following schemes and elsewhere herein are:

| | |
|---|---|
| $Ac_2O$ | Acetic anhydride |
| ACN | Acetonitrile |
| AcOH/HOAc | Glacial acetic acid |
| δ | chemical shift |
| DCM | Dichloromethane or methylene chloride |
| DCE | 1,2-Dichloroethane |
| DEAD | Diethyl azodicarboxylate |
| DIAD | Diisopropyl azodicarboxylate |
| DIEA | N,N-Diisopropylethylamine |
| DMA | N,N-Dimethylacetamide |
| DME | Dimethoxyethane |
| DMF | N,N-Dimethylformamide |
| DMP | Dess-Martin Periodinane |
| DMSO | Dimethylsulfoxide |
| $(COCl)_2$ | Oxalyl chloride |
| EDCI | N-(3-Dimethylaminopropyl)-N'-ethylcarbodiimide hydrochloride |
| EDTA | Ethylenediaminetetraacetic acid |
| ee | enantiomeric excess |
| h | Hour |
| $^1H$ NMR | proton nuclear magnetic resonance |
| HATU | 2-(3H-[1,2,3]Triazolo[4,5-b]pyridin-3-yl)-1,1,3,3-tetramethylisouronium hexafluorophosphate |
| HOBT | 1H-Benzo[d][1,2,3]triazol-1-ol hydrate |
| HPLC | high performance liquid chromatography |
| Hz | Hertz |
| LCMS | liquid chromatography/mass spectrometry |
| MeOH | Methanol |
| min | Minutes |
| MS | mass spectrometry |
| NMM | 4-Methylmorpholine |

-continued

| | |
|---|---|
| NMP | N-Methyl-2-pyrrolidone |
| rt | room temperature |
| Rt | retention time |
| TEA | Triethylamine |
| TFA | Trifluoroacetic acid |
| THF | Tetrahydrofuran |
| TLC | thin layer chromatography |
| LiOH | Lithium hydroxide |
| NaOH | Sodium hydroxide |
| $Cs_2CO_3$ | Cesium carbonate |
| HCl | Hydrochloric acid |
| $NH_4HCO_3$ | Ammonium bicarbonate |
| PE | Petroleum ether |
| EtOAc | Ethyl acetate |
| Na2SO4 | Sodium sulfate |

Example 1

Synthesis of N-(4-[[(1S)-1-(4-chlorophenyl)-2-(pyrrolidin-1-yl)ethyl]carbamoyl]-1,2,3-thiadiazol-5-yl)-5-(trifluoromethyl)pyridine-3-carboxamide and N-(4-[[(1R)-1-(4-chlorophenyl)-2-(pyrrolidin-1-yl)ethyl]carbamoyl]-1,2,3-thiadiazol-5-yl)-5-(trifluoromethyl)pyridine-3-carboxamide (16)

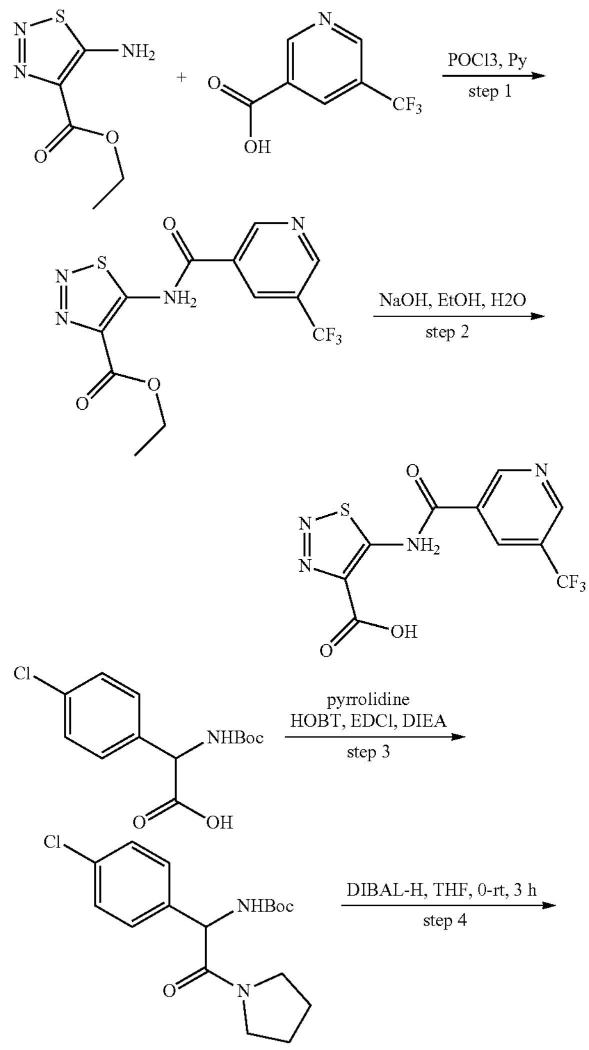

-continued

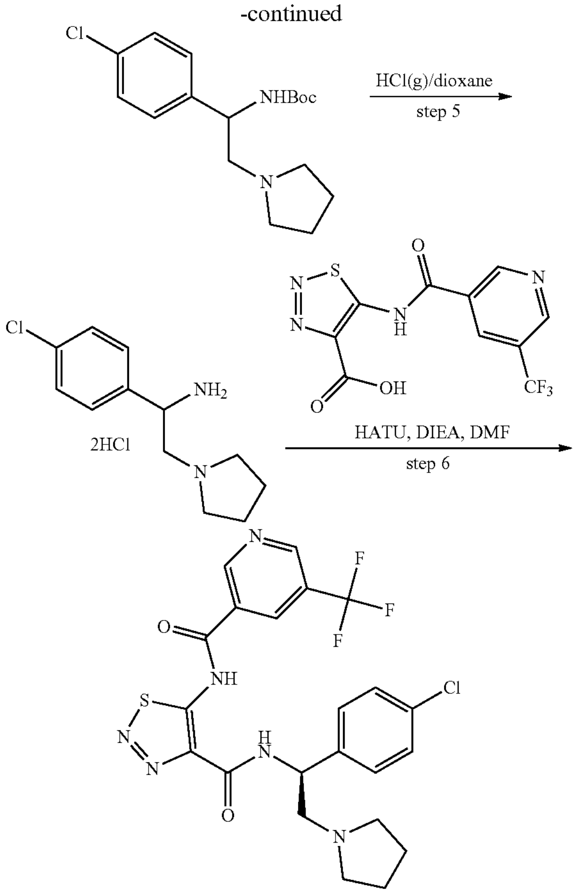

first eluting isomer

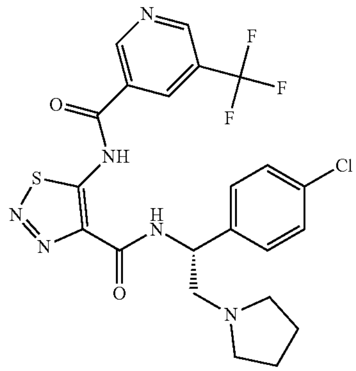

second eluting isomer
16

Step 1. Ethyl 5-[5-(trifluoromethyl)pyridine-3-amido]-1,2,3-thiadiazole-4-carboxylate To a stirred mixture of ethyl 5-amino-1,2,3-thiadiazole-4-carboxylate (1.50 g, 8.66 mmol) and 5-(trifluoromethyl) pyridine-3-carboxylic acid (1.99 g, 10.4 mmol) in Pyridine (40 mL) was added POCl3 (11.0 mL, 113 mmol) dropwise at 0° C. under nitrogen atmosphere. The resulting mixture was stirred for 2 hours at 25° C. under nitrogen atmosphere. The reaction mixture was poured into water/ice (100 mL). The mixture was basified pH 8 with saturated $NaHCO_3$ (aq.) at 0° C. The resulting mixture was extracted with $CH_2Cl_2$ (3×600 mL). The combined organic layers were washed with 1M HCl (600 mL), dried over anhydrous Na2SO4, filtered and concentrated under reduced pressure. The residue was purified by silica gel column chromatography, eluted with PE/EtOAc (2:1) to afford ethyl 5-[5-(trifluoromethyl)pyridine-3-amido]-1,2,3-thiadiazole-4-carboxylate (1.10 g, 37%) as a yellow solid. LCMS (ES, m/z): 347 $[M+H]^+$.

Step 2. 5-[5-(trifluoromethyl)pyridine-3-amido]-1,2,3-thiadiazole-4-carboxylic acid To a solution of ethyl 5-[5-(trifluoromethyl)pyridine-3-amido]-1,2,3-thiadiazole-4-carboxylate (1.10 g, 3.17 mmol) in EtOH (60 mL) was added NaOH (8 mol/L in water) (60 mL). The resulting mixture was stirred for 2 h at 25° C. The mixture was acidified to pH 3 with 1M HCl at 0° C. The volatile was evaporated. The solids were collected by filtration, washed with water (100 mL) and dried under infrared light. This resulted in 5-[5-(trifluoromethyl)pyridine-3-amido]-1,2,3-thiadiazole-4-carboxylic acid (1 g, 96%) as a white solid. LCMS (ES, m/z): 319 $[M+H]^+$.

Step 3. Tert-butyl N-[1-(4-chlorophenyl)-2-oxo-2-(pyrrolidin-1-yl)ethyl]carbamate To a stirred mixture of [(tert-butoxycarbonyl)amino](4-chlorophenyl)acetic acid (500 mg, 1.75 mmol), HOBT (476 mg, 3.52 mmol), EDCI (674 mg, 3.52 mmol) and DIEA (701 mg, 5.42 mmol) in DMF (5 mL) was added pyrrolidine (200 mg, 2.81 mmol). The resulting mixture was stirred for 2 hours at 26° C. The resulting mixture was poured into water (20 mL) and extracted with EtOAc (3×20 mL). The combined organic layers were washed with brine (50 mL), dried over anhydrous $Na_2SO_4$, filtered and concentrated under reduced pressure. The residue was purified by reverse flash chromatography with the following conditions: column, $C_{18}$ silica gel, 80 g, 20-35 um; mobile phase, water with 0.1% FA and ACN (0% to 80% gradient in 50 min); detector, UV 254 nm. This is to afford tert-butyl N-[1-(4-chlorophenyl)-2-oxo-2-(pyrrolidin-1-yl)ethyl]carbamate (400 mg, 64%) as a yellow oil. LCMS (ES, m/z): 339, 341 $[M+H]^+$.

Step 4. Tert-butyl N-[1-(4-chlorophenyl)-2-(pyrrolidin-1-yl)ethyl]carbamate

To a stirred solution of tert-butyl N-[1-(4-chlorophenyl)-2-oxo-2-(pyrrolidin-1-yl)ethyl]carbamate (300 mg, 0.84 mmol) in THF (10 mL) was added DIBA1-H (1 mol/L in hexane) (10 mL, 9.92 mmol) dropwise at 0° C. under nitrogen atmosphere. The resulting mixture was stirred for 3 hours at 25° C. The resulting mixture was poured into water (100 mL) and extracted with EtOAc (3×100 mL). The combined organic layers were washed with brine (200 mL), dried over anhydrous $Na_2SO_4$, filtered and concentrated under reduced pressure. The residue was purified by reverse flash chromatography with the following conditions: column, $C_{18}$ silica gel, 80 g, 20-35 um; mobile phase, water with 0.1% FA and ACN (0% to 100% gradient in 30 min); detector, UV 254 nm. The product fractions were concentrated under vacuum to afford tert-butyl N-[1-(4-chlorophenyl)-2-(pyrrolidin-1-yl)ethyl]carbamate (150 mg, 52%) as a yellow oil. LCMS (ES, m/z): 325, 327 $[M+H]^+$.

Step 5. 1-(4-Chlorophenyl)-2-(pyrrolidin-1-yl)ethanamine dihydrochloride

To a stirred solution of tert-butyl N-[1-(4-chlorophenyl)-2-(pyrrolidin-1-yl)ethyl]carbamate (180 mg, 0.55 mmol) in 1,4-dioxane (1 mL) was added HCl (gas) in 1,4-dioxane (4 M, 2 mL) at 0° C. The resulting mixture was stirred for 1 hour at 26° C. The mixture was concentrated under vacuum to afford 1-(4-chlorophenyl)-2-(pyrrolidin-1-yl)ethanamine dihydrochloride (150 mg, 86%) as a white solid. The product was used in the next step without further purification. LCMS (ES, m/z): 225, 227 $[M-2HCl+H]^+$.

Step 6. N-(4-[[(1S)-1-(4-chlorophenyl)-2-(pyrrolidin-1-yl)ethyl]carbamoyl]-1,2,3-thiadiazol-5-yl)-5-(trifluoromethyl)pyridine-3-carboxamide and N-(4-[[(1R)-1-(4-chlorophenyl)-2-(pyrrolidin-1-yl)ethyl]carbamoyl]-1,2,3-thiadiazol-5-yl)-5-(trifluoromethyl)pyridine-3-carboxamide (16)

To a stirred mixture of 5-[5-(trifluoromethyl)pyridine-3-amido]-1,2,3-thiadiazole-4-carboxylic acid (157 mg, 0.48 mmol) in DMF (3 mL) was added HATU (372 mg, 0.96 mmol), DIEA (316 mg, 2.39 mmol) and 1-(4-chlorophenyl)-2-(pyrrolidin-1-yl)ethanamine dihydrochloride (150 mg, 0.48 mmol). The resulting mixture was stirred for 2 hours at 26° C. The resulting mixture was poured into water (10 mL) and extracted with EtOAc (3×10 mL). The combined organic layers were washed with brine (2×20 mL), dried over anhydrous $Na_2SO_4$, filtered and concentrated under reduced pressure. The residue was purified by reverse flash chromatography with the following conditions: column, $C_{18}$ silica gel, 40 g, 20-35 um; mobile phase, water with 0.1% FA and ACN (0% to 80% gradient in 30 min); detector, UV 254 nm. The product fractions were concentrated under vacuum to give the racemic product. The reacmate was separated by prep chiral HPLC with the following condition (Column: CHIRALPAK IG, 2×25 cm, 5 μm; Mobile Phase A: Hex (0.1% TEA), Mobile Phase B: EtOH; Flow rate: 20 mL/min; Gradient: 30 B to 30 B in 13.5 min; 220/254 nm; RT1: 6.837; RT2: 11.035). The product fractions were concentrated under vacuum and then dissolved in ACN (5 mL) and $H_2O$ (5 mL). The mixture was lyophilized to afford the first eluting isomer of N-(4-[[(1S)-1-(4-chlorophenyl)-2-(pyrrolidin-1-yl)ethyl]carbamoyl]-1,2,3-thiadiazol-5-yl)-5-(trifluoromethyl)pyridine-3-carboxamide (11.3 mg, 4%) as a white solid. And the second eluting isomer of N-(4-[[(1R)-1-(4-chlorophenyl)-2-(pyrrolidin-1-yl)ethyl]carbamoyl]-1,2,3-thiadiazol-5-yl)-5-(trifluoromethyl)pyridine-3-carboxamide (12.4 mg, 5%) as a white solid.

First Eluting Isomer: $^1$H-NMR (DMSO-d6, 400 MHz) δ (ppm): 10.46 (br s, 1H), 9.47 (br s, 2H), 9.10 (s, 1H), 8.59 (s, 1H), 7.65 (d, J=6.8 Hz, 2H), 7.48 (d, J=8.4 Hz, 2H), 5.78 (br s, 1H), 3.85-3.38 (m, 6H), 2.05-1.98 (m, 4H). LCMS (ES, m/z): 525, 527 $[M+H]^+$.

Second Eluting Isomer (16): $^1$H-NMR (DMSO-d6, 400 MHz) δ (ppm): 10.46 (br s, 1H), 9.51-9.38 (m, 2H), 9.10 (s, 1H), 8.59 (s, 1H), 7.64 (d, J=7.6 Hz, 2H), 7.48 (d, J=2 Hz, 2H), 5.78 (br s, 1H), 3.84-3.40 (m, 6H), 2.02-1.90 (m, 4H). LCMS (ES, m/z): 525, 527 $[M+H]^+$.

Example 2

Synthesis of 2-(4-chlorobenzenesulfonamido)-N-(4-phenyl-1,3-thiazol-2-yl)-4-(trifluoromethyl)benzamide (17)

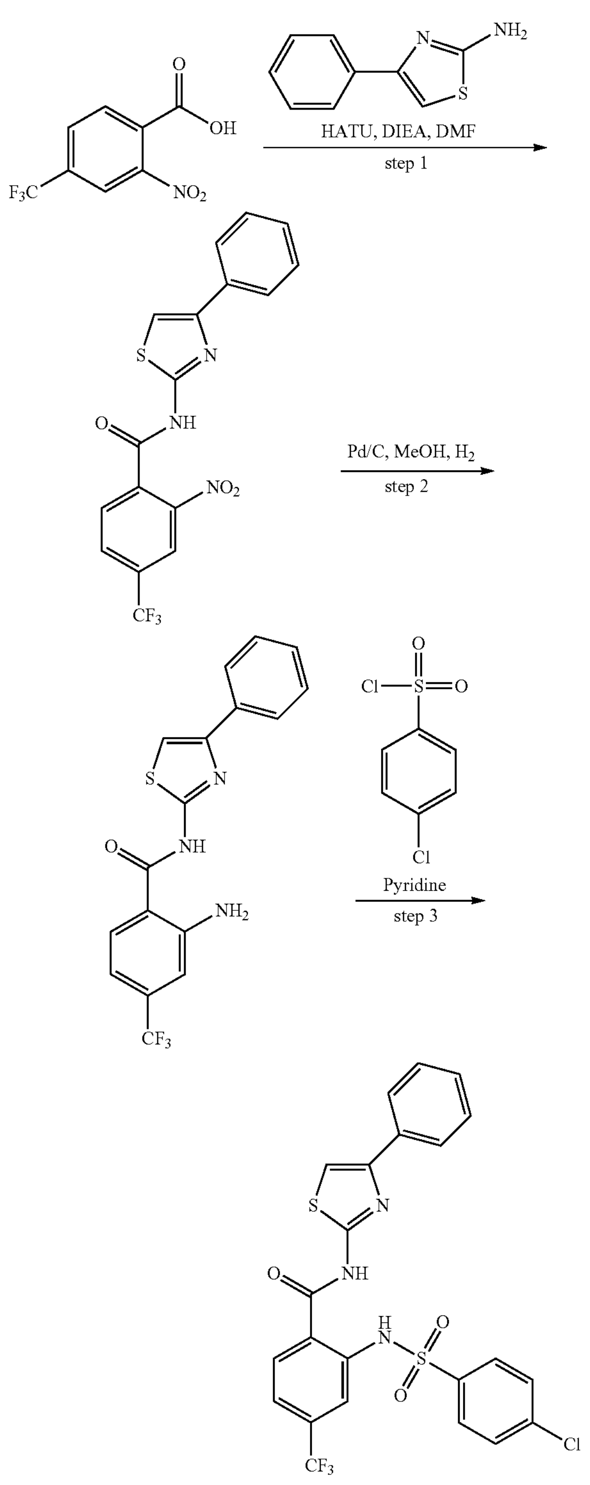

17

Step 1. 2-nitro-N-(4-phenylthiazol-2-yl)-4-(trifluoromethyl)benzamide

To a stirred mixture of 2-nitro-4-(trifluoromethyl)benzoic acid (5.00 g, 21.3 mmol) and HATU (12.0 g, 31.6 mmol) in DMF (30 mL) were added DIEA (10.2 mL, 61.9 mmol) and 4-phenylthiazol-2-amine (4.00 g, 22.7 mmol) at 0° C. The resulting mixture was stirred for 2 h at 25° C. The mixture was diluted with water/ice (100 mL) and extracted with DCM (3x10 mL). The combined organic layers were washed with brine (3x100 mL) and dried over anhydrous $Na_2SO_4$. After filtration, the filtrate was concentrated under reduced pressure. The residue was purified by silica gel column chromatography, eluted with PE/EtOAc (1:1) to afford 2-nitro-N-(4-phenyl-1,3-thiazol-2-yl)-4-(trifluoromethyl)benzamide (2.00 g, 23%) as a light brown solid. LCMS (ES, m/z): 394 $[M+H]^+$.

Step 2. 2-amino-N-(4-phenyl-1,3-thiazol-2-yl)-4-(trifluoromethyl)benzamide

A mixture of 2-nitro-N-(4-phenylthiazol-2-yl)-4-(trifluoromethyl)benzamide (2.00 g, 5.08 mmol) and Pd/C (200 mg, 10%) in MeOH (50 mL) was stirred for 2 h at 25° C. under hydrogen atmosphere. The solids were filtered out and the filtrate was concentrated under reduced pressure. The crude product was purified by reverse phase column (column, $C_{18}$ silica gel; mobile phase, water with FA (0.1%) and ACN (10% to 50% gradient in 40 min); detector, UV 254/220 nm) to afford 2-amino-N-(4-phenyl-1,3-thiazol-2-yl)-4-(trifluoromethyl)benzamide (1.07 g, 54%) as a dark yellow solid. LCMS (ES, m/z): 364 $[M+H]^+$.

Step 3. 2-(4-chlorobenzenesulfonamido)-N-(4-phenyl-1,3-thiazol-2-yl)-4-(trifluoromethyl)benzamide (17)

A mixture of 2-amino-N-(4-phenyl-1,3-thiazol-2-yl)-4-(trifluoromethyl)benzamide (100 mg, 0.27 mmol) and 4-chlorobenzene-1-sulfonyl chloride (290 mg, 1.37 mmol) in pyridine (5 mL) was stirred for 5 h at 60° C. The mixture was cooled to room temperature, diluted with water/ice (20 mL) and extracted with DCM (3x10 mL). The combined organic layers were washed with brine (30 mL) and dried over anhydrous $Na_2SO_4$. After filtration, the filtrate was concentrated under reduced pressure. The residue was purified by reverse flash chromatography with the following conditions: column, $C_{18}$ silica gel, 80 g, 20-35 um; mobile phase, water (0.1% FA) and ACN (0% to 100% in 30 min); detector, UV 254/220 nm. The collected fraction was lyophilized to afford 2-(4-chlorobenzenesulfonamido)-N-(4-phenyl-1,3-thiazol-2-yl)-4-(trifluoromethyl)benzamide (23.1 mg, 16%) as a white solid.

$^1H$ NMR (400 MHz, DMSO-d6) δ (ppm): 12.89 (br s, 1H), 10.44 (br s, 1H), 7.96-7.91 (m, 3H), 7.79-7.66 (m, 4H), 7.57 (d, J=8.4 Hz, 2H), 7.49-7.45 (m, 3H), 7.38-7.34 (m, 1H). LCMS (ES, m/z): 538,540 $[M+H]^+$.

Example 3

Synthesis of 5-(3-chlorobenzamido)-N-[2-(3-chlorophenyl)propan-2-yl]-1,2,3-thiadiazole-4-carboxamide (18)

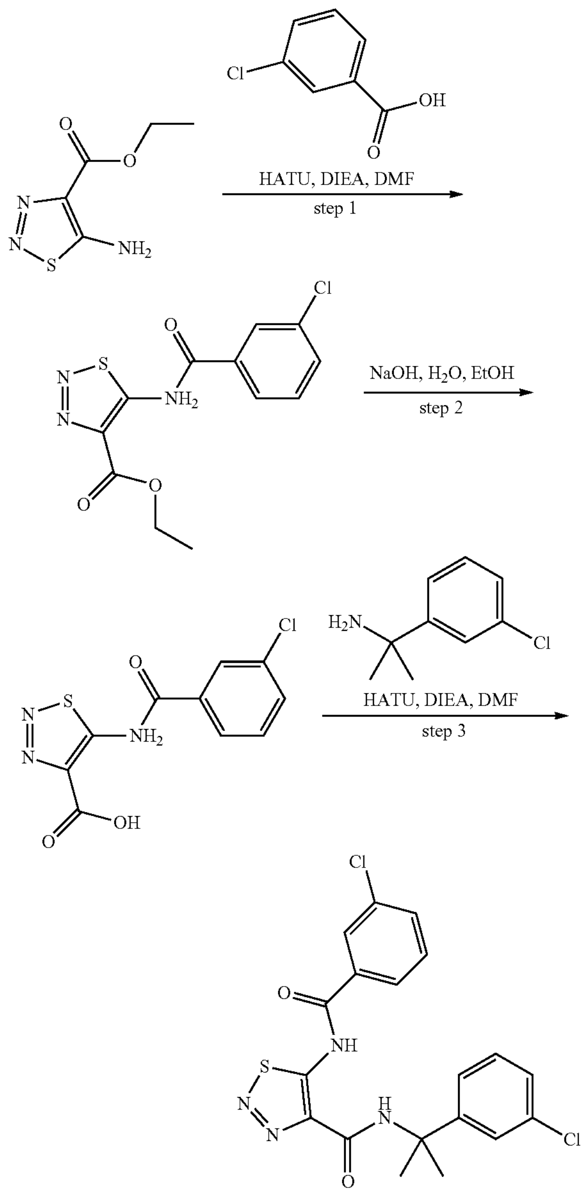

18

Step 1. ethyl 5-(3-chlorobenzamido)-1,2,3-thiadiazole-4-carboxylate

To the mixture of 3-chlorobenzoic acid (2.20 g, 13.2 mmol) and HATU (5.00 g, 13.2 mmol) in DMF (60 mL) was added ethyl 5-amino-1,2,3-thiadiazole-4-carboxylate (2.00 g, 11.0 mmol) and DIEA (5.90 mL, 32.9 mmol) dropwise at 0° C. The reaction mixture was stirred for 3 h at room temperature. The mixture was diluted with water (30 mL) and extracted with EtOAc (3×50 mL). The combined organic layers were washed with brine (2×30 mL), dried over anhydrous $Na_2SO_4$ and concentrated under reduced pressure. The residue was purified by silica gel column chromatography, eluted with PE/EtOAc (1:1) to afford ethyl 5-(3-chlorobenzamido)-1,2,3-thiadiazole-4-carboxylate as a white solid (2.50 g, 73%). LCMS (ES, m/z): 312, 314 $[M+H]^+$.

Step 2. 5-(3-chlorobenzamido)-1,2,3-thiadiazole-4-carboxylic acid

A mixture of ethyl 5-(3-chlorobenzamido)-1,2,3-thiadiazole-4-carboxylate (2.50 g, 7.62 mmol) and NaOH (0.60 g, 15.0 mmol) in $H_2O$ (20 mL) and EtOH (30 mL) was stirred for 16 h at 25° C. The resulting mixture was partially concentrated under reduced pressure. The mixture was acidified to pH 3 with HCl (1N). The precipitated solid was collected by filtration, washed with water (10 mL) and dried under vacuum to afforded 5-(3-chlorobenzamido)-1,2,3-thiadiazole-4-carboxylic acid as a white solid (2.00 g, 88%). LCMS (ES, m/z): 284, 286 $[M+H]^+$.

Step 3. 5-(3-chlorobenzamido)-N-[2-(3-chlorophenyl)propan-2-yl]-1,2,3-thiadiazole-4-carboxamide (18)

To a stirred mixture of 5-(3-chlorobenzamido)-1,2,3-thiadiazole-4-carboxylic acid (200 mg, 0.63 mmol) and HATU (361 mg, 0.94 mmol) in DMF (5 mL) were added 2-(3-chlorophenyl)propan-2-amine (129 mg, 0.76 mmol) and DIEA (315 uL, 1.90 mmol) dropwise at 0° C. The resulting mixture was stirred for 1 h at 25° C. The mixture was diluted with water (15 mL) and extracted with EtOAc (3×15 mL). The combined organic layers were washed with brine (15 mL), dried over anhydrous $Na_2SO_4$ and concentrated under reduced pressure. The residue was purified by silica gel column chromatography, eluted with PE/EtOAc (1:1). The crude product was purified by Prep-HPLC with the following conditions: Column, XBridge Shield RP18 OBD Column, 30×150 mm, 5 um; mobile phase, A: water (10 mmol/L $NH_4HCO_3$) and B: ACN (30% to 60% in 7 min); Detector, UV 254 nm. The product fractions (RT: 6.44 min) were lyophilized to afford 5-(3-chlorobenzamido)-N-[2-(3-chlorophenyl)propan-2-yl]-1,2,3-thiadiazole-4-carboxamide as a white solid (53.6 mg, 19%).

$^1$H-NMR (DMSO, 400 MHz) δ (ppm): 12.13 (s, 1H), 9.21 (s, 1H), 7.90 (br s, 1H), 7.85-7.75 (m, 2H), 7.70-7.59 (m, 1H), 7.52 (s, 1H), 7.50-7.45 (m, 1H), 7.38-7.34 (m, 1H), 7.28-7.27 (m, 1H), 1.79 (s, 6H). LCMS (ES, m/z): 435, 437 $[M+H]^+$.

Example 4

Synthesis of N-[(4-chlorophenyl)methyl]-5-[3-(trifluoromethyl)benzamido]-1, 2, 3-thiadiazole-4-carboxamide (24)

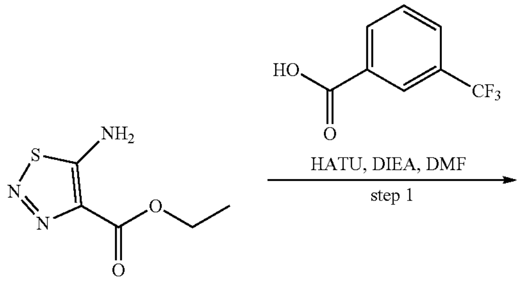

-continued

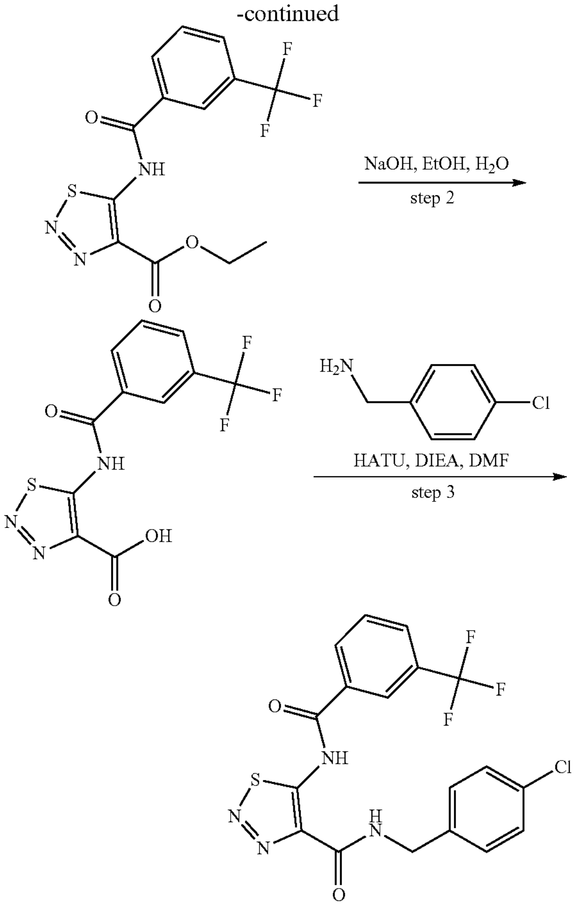

24

Step 1. ethyl 5-[3-(trifluoromethyl)benzamido]-1,2,3-thiadiazole-4-carboxylate

To a stirred mixture of 3-(trifluoromethyl)benzoic acid (177 mg, 0.93 mmol) and HATU (444 mg, 1.16 mmol) in DMF (9 mL) was added ethyl 5-amino-1,2,3-thiadiazole-4-carboxylate (150 mg, 0.87 mmol) and DIEA (386 uL, 2.33 mmol) dropwise at 0° C. The resulting mixture was stirred for 16 h at 25° C. The reaction was quenched by the addition of water (10 mL) at room temperature. The solids were collected by filtration, washed with water (3×7 mL) and dried under UV light to afford ethyl 5-[3-(trifluoromethyl) benzamido]-1,2,3-thiadiazole-4-carboxylate as a yellow solid (160 mg, 50%). LCMS (ES, m/z): 346 $[M+H]^+$.

Step 2. 5-[3-(trifluoromethyl)benzamido]-1,2,3-thiadiazole-4-carboxylic acid

To a stirred mixture of NaOH (66 mg, 1.65 mmol) in EtOH (3 mL) and $H_2O$ (3 mL) was added ethyl 5-[3-(trifluoromethyl)benzamido]-1,2,3-thiadiazole-4-carboxylate (160 mg, 0.46 mmol) in portions at 0° C. The resulting mixture was stirred for 3 h at 25° C. The resulting mixture was partially concentrated under reduced pressure. The mixture was acidified to pH 6 with HCl (1N). The precipitated solids were collected by filtration, washed with water (10 mL) and dried under UV light to afford 5-[3-(trifluoromethyl)benzamido]-1,2,3-thiadiazole-4-carboxylic acid as an off-white solid (100 mg, 68%). LCMS (ES, m/z): 318 $[M+H]^+$.

Step 3. N-[(4-chlorophenyl)methyl]-5-[3-(trifluoromethyl)benzamido]-1,2,3-thiadiazole-4-carboxamide (24)

To a stirred mixture of 5-[3-(trifluoromethyl)benzamido]-1,2,3-thiadiazole-4-carboxylic acid (100 mg, 0.31 mmol) in DMF (3 mL) was added HATU (170 mg, 0.44 mmol), 1-(4-chlorophenyl)methanamine (51 mg, 0.36 mmol) and DIEA (150 µl, L, 0.89 mmol) at 0° C. The resulting mixture was stirred for 4 h at 25° C. The mixture was diluted with water (15 mL) and extracted with $CH_2Cl_2$ (3×10 mL). The combined organic layers were washed with brine (15 mL), dried over anhydrous $Na_2SO_4$ and concentrated under reduced pressure. The crude product was purified by Prep-HPLC Column, XBridge Prep $C_{18}$ OBD Column, 5 um, 19×150 mm; mobile phase, A: water (containing 0.05% TFA) and ACN (55% to 85% in 7 min); Detector, UV 254 nm. The product fractions (RT: 6.68 min) were lyophilized to afford N-[(4-chlorophenyl)methyl]-5-[3-(trifluoromethyl) benzamido]-1,2,3-thiadiazole-4-carboxamide as an off-white solid (33 mg, 24%).

$^1$H-NMR (DMSO, 400 MHz) δ (ppm): 9.42 (br s, 1H), 8.04-8.00 (m, 2H), 7.95-7.90 (m, 1H), 7.76-7.72 (m, 1H), 7.69-7.47 (m, 1H), 7.44-7.29 (m, 4H), 4.52 (d, J=6.4 Hz, 2H). LCMS (ES, m/z): 441,443 $[M+H]^+$.

Example 5

Synthesis of N-(5-chloro-2,3-dihydro-1H-inden-2-yl)-5-[2-chloro-3-(trifluoromethyl) benzamido]-1,2,3-thiadiazole-4-carboxamide (25)

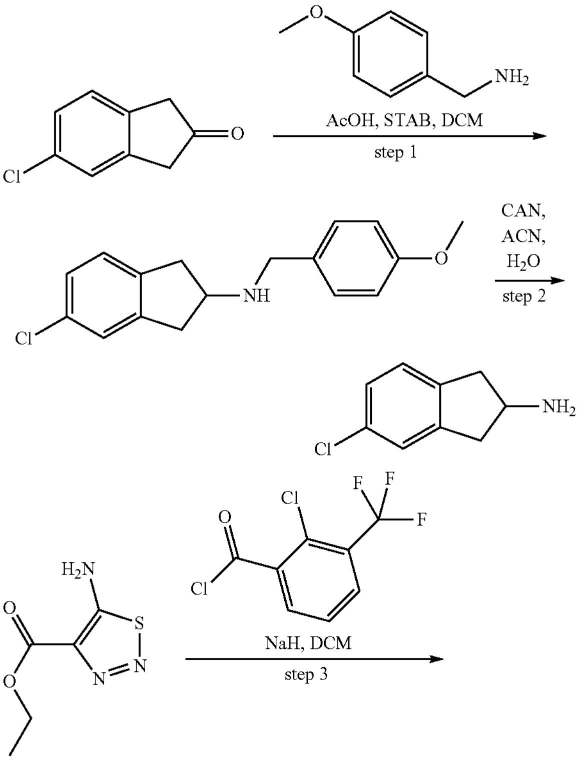

-continued

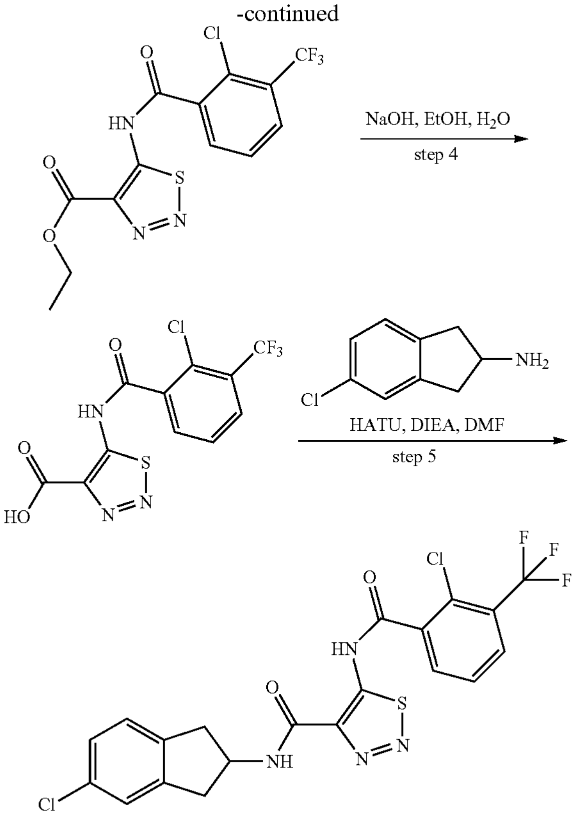

26

Step 1. 5-chloro-N-[(4-methoxyphenyl)methyl]-2,3-dihydro-1H-inden-2-amine

To a stirred mixture of 5-chloro-2,3-dihydro-1H-inden-2-one (200 mg, 1.20 mmol), 4-methoxybenzylamine (247 mg, 1.80 mmol) in DCM (5 mL) was added AcOH (0.1 mL) and STAB (763 mg, 3.60 mmol). The reaction mixture was stirred for 16 h at 25° C. The resulting mixture was diluted with water (10 mL) and extracted with $CH_2Cl_2$ (3x10 mL). The combined organic layers were washed with brine (10 mL), dried over anhydrous Na2$SO_4$ and concentrated under reduced pressure. The residue was purified by silica gel column chromatography, eluted with PE/EtOAc (1:1) to afford 5-chloro-N-[(4-methoxyphenyl)methyl]-2,3-dihydro-1H-inden-2-amine as a yellow solid (140 mg, 41%). LCMS (ES, m/z): 288, 290 $[M+H]^+$.

Step 2. 5-chloro-2,3-dihydro-JH-inden-2-amine

A mixture of 5-chloro-N-[(4-methoxyphenyl)methyl]-2,3-dihydro-1H-inden-2-amine (120 mg, 0.42 mmol) and $(NH_4)_2Ce(NO_3)_6$ (86 mg, 0.16 mmol) in ACN (2 mL) and $H_2O$ (0.5 mL) was stirred for 16 h at 25° C. under nitrogen atmosphere. The resulting mixture was diluted with water (5 mL) and extracted with EtOAc (3x5 mL). The combined organic layers were washed with brine (10 mL), dried over anhydrous $Na_2SO_4$ and concentrated under reduced pressure. The residue was purified by reverse flash chromatography with the following conditions: column, $C_{18}$ silica gel (80 g, 20 um); mobile phase, water (containing 0.05% TFA), ACN (0% to 80% in 30 min); detector, UV 254 nm. The collected fraction was concentrated to afford 5-chloro-2,3-dihydro-1H-inden-2-amine as a yellow solid (30 mg, 42%). LCMS (ES, m/z): 168,170 $[M+H]^+$.

Step 3. ethyl 5-[2-chloro-3-(trifluoromethyl)benzamido]-1,2,3-thiadiazole-4-carboxylate To a stirred mixture of ethyl 5-amino-1,2,3-thiadiazole-4-carboxylate (100 mg, 0.52 mmol) in DCM (5 mL) was added NaH (24 mg, 0.60 mmol, 60%) at 0° C., after stirred for 10 min, to the above mixture was added 2-chloro-3-(trifluoromethyl)benzoyl chloride (151 mg, 0.59 mmol) in DCM (1 mL) dropwise at 0° C. The resulting mixture was stirred for 16 h at 25° C. under nitrogen atmosphere. The mixture was then poured into water (5 mL) and extracted with EtOAc (3x5 mL). The combined organic layers were washed with brine (8 mL), dried over anhydrous $Na_2SO_4$ and concentrated under reduced pressure. The residue was purified by silica gel column chromatography, eluted with PE/EtOAc (2:1) to afford ethyl 5-[2-chloro-3-(trifluoromethyl)benzamido]-1,2,3-thiadiazole-4-carboxylate as a white solid (120 mg, 54%). LCMS (ES, m/z): 380,382 $[M+H]^+$.

Step 4. 5-[2-chloro-3-(trifluoromethyl)benzamido]-1,2,3-thiadiazole-4-carboxylic acid A mixture of ethyl 5-[2-chloro-3-(trifluoromethyl)benzamido]-1,2,3-thiadiazole-4-carboxylate (120 mg, 0.40 mmol) and NaOH (32 mg, 0.81 mmol) in EtOH (3 mL) and $H_2O$ (1 mL) was stirred for 16 h at 25° C. The resulting mixture was acidified to pH 5 with HCl (1 N) and extracted with EtOAc (3x5 mL). The combined organic layers were washed with brine (2x8 mL), dried over anhydrous $Na_2SO_4$ and concentrated under reduced pressure. The residue was purified by reverse flash chromatography column, $C_{18}$ silica gel; mobile phase, water (containing 0.1% TFA) and ACN (0% to 90% 30 min); detector, UV 254 nm. The collected fraction was concentrated to afford 5-[2-chloro-3-(trifluoromethyl)benzamido]-1,2,3-thiadiazole-4-carboxylic acid as a white solid (100 mg, 69%). LCMS (ES, m/z): 352,354 $[M+H]^+$.

Step 5. N-(5-chloro-2,3-dihydro-1H-inden-2-yl)-5-[2-chloro-3-(trifluoromethyl)benzamido]-1,2,3-thiadiazole-4-carboxamide (25)

A mixture of 5-[2-chloro-3-(trifluoromethyl)benzamido]-1,2,3-thiadiazole-4-carboxylic acid (30 mg, 0.08 mmol), HATU (44 mg, 0.12 mmol), 5-chloro-2,3-dihydro-1H-inden-2-amine (15 mg, 0.09 mmol) and DIEA (29 mg, 0.23 mmol) in DMF (3 mL) was stirred for 16 h at 25° C. The resulting mixture was diluted with water (5 mL) and extracted with EtOAc (3x5 mL). The combined organic layers were washed with brine (10 mL), dried over anhydrous $Na_2SO_4$ and concentrated under reduced pressure. The residue was purified by reverse flash chromatography with the following conditions: column, $C_{18}$ silica gel (40 g, 20-35 um); mobile phase, A: water (containing 0.1% FA), B: ACN (0% to 60% in 30 min); detector, UV 254 nm. The product fractions were lyophilized to afford N-(5-chloro-2,3-dihydro-1H-inden-2-yl)-5-[2-chloro-3-(trifluoromethyl)benzamido]-1,2,3-thiadiazole-4-carboxamide as an off-white solid (12 mg, 29%).

$^1$H-NMR ($CD_3OD$, 400 MHz) δ (ppm): 8.09-8.07 (m, 2H), 7.75-7.71 (m, 1H), 7.26-7.17 (m, 3H), 4.99-4.91 (m, 1H), 3.40-3.38 (m, 2H), 3.14-3.01 (m, 2H). LCMS (ES, m/z): 501, 503 $[M+H]^+$.

Example 6

Synthesis of (S)—N-(5-chloro-2,3-dihydro-1H-inden-2-yl)-5-(5-(trifluoromethyl)nicotinamido)-1,2,3-thiadiazole-4-carboxamide (first eluting isomer) and (R)—N-(5-chloro-2,3-dihydro-1H-inden-2-yl)-5-(5-(trifluoromethyl)nicotinamido)-1,2,3-thiadiazole-4-carboxamide (second eluting isomer) (29)

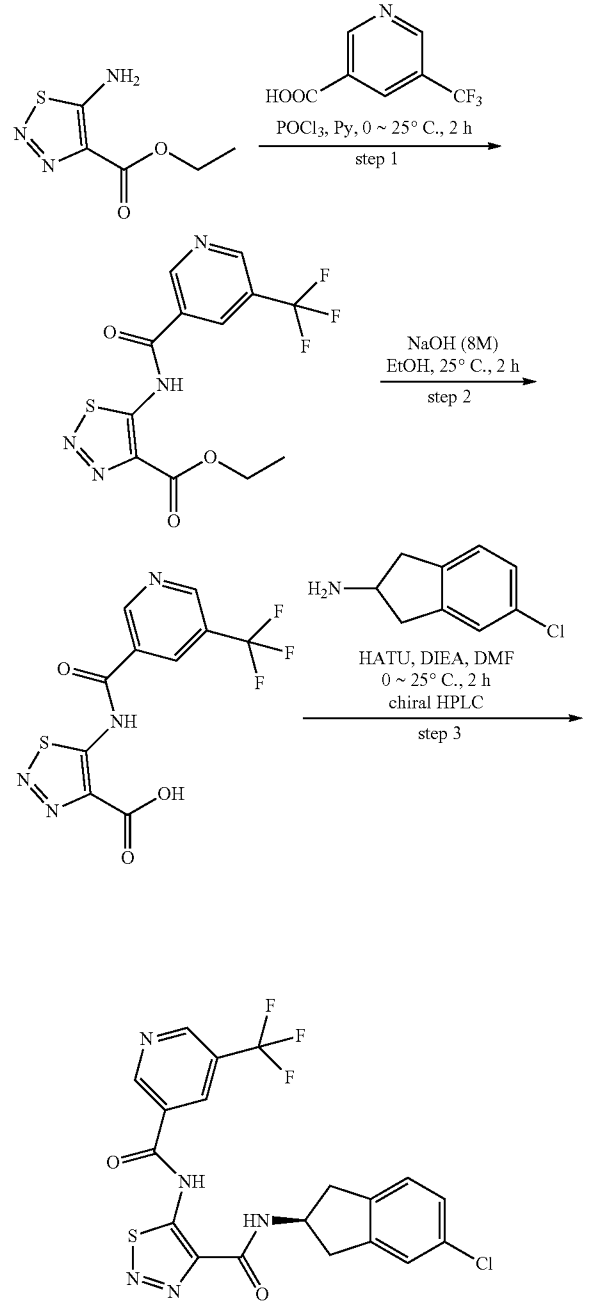

First eluting isomer

-continued

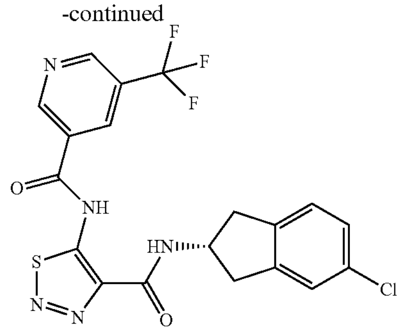

second eluting isomer
29

Step 1. ethyl 5-(5-(trifluoromethyl)nicotinamido)-1,2,3-thiadiazole-4-carboxylate To a stirred mixture of ethyl 5-amino-1,2,3-thiadiazole-4-carboxylate (400 mg, 2.31 mmol) and 5-(trifluoromethyl)pyridine-3-carboxylic acid (530 mg, 2.77 mmol) in Pyridine (20 mL) were added $POCl_3$ (2.80 mL, 30.0 mmol) dropwise at 0° C. The resulting mixture was stirred for 2 h at 25° C. The resulting mixture was concentrated under reduced pressure. The residue was diluted with water/ice (20 mL), the mixture was basified to pH 8 with saturated $NaHCO_3$ (aq.) and extracted with EtOAc (3×50 mL). The combined organic layers were washed with brine (100 mL), dried over anhydrous $Na_2SO_4$ and concentrated under reduced pressure. The residue was purified by silica gel column chromatography, eluted with PE/EtOAc (1:1) to afford ethyl 5-(5-(trifluoromethyl)nicotinamido)-1,2,3-thiadiazole-4-carboxylate (610 mg, 71%) as a yellow solid. LCMS (ES, m/z): 347 $[M+H]^+$.

Step 2. 5-(5-(trifluoromethyl)nicotinamido)-1, 2, 3-thiadiazole-4-carboxylic acid A mixture of ethyl 5-[5-(trifluoromethyl)pyridine-3-amido]-1,2,3-thiadiazole-4-carboxylate (600 mg, 1.73 mmol) in NaOH (8M) (20 mL) and EtOH (20 mL) was stirred for 2 h at 25° C. The resulting mixture was partially concentrated under reduced pressure. The mixture was acidified to pH 3 with 1M HCl at 0° C. The solids were collected by filtration, washed with water (3×20 mL) and dried under infrared light. This resulted in 5-(5-(trifluoromethyl)nicotinamido)-1,2,3-thiadiazole-4-carboxylic acid (500 mg, 83%) as a white solid. LCMS (ES, m/z): 319 $[M+H]^+$.

Step 3. (S)—N-(5-chloro-2,3-dihydro-1H-inden-2-yl)-5-(5-(trifluoromethyl)nicotinamido)-1,2,3-thiadiazole-4-carboxamide (first eluting isomer) and (R)—N-(5-chloro-2,3-dihydro-1H-inden-2-yl)-5-(5-(trifluoromethyl)nicotinamido)-1,2,3-thiadiazole-4-carboxamide (second eluting isomer) (29)

To a stirred mixture of 5-[5-(trifluoromethyl)pyridine-3-amido]-1,2,3-thiadiazole-4-carboxylic acid (70 mg, 0.22 mmol) in DMF (2 mL) was added HATU (126 mg, 0.33 mmol), DIEA (0.11 mL, 0.66 mmol) and 5-chloro-2,3-dihydro-1H-inden-2-amine (44 mg, 0.26 mmol) at 0° C. The resulting mixture was stirred for 2 h at 25° C. The mixture was poured into water (20 mL) and extracted with EtOAc (3×20 mL). The combined organic layers were washed with brine (50 mL), dried over anhydrous $Na_2SO_4$ and concentrated under reduced pressure. The residue was purified by silica gel column chromatography, eluted with PE/EtOAc (1:2) to afford the racemic product. The racemate was separated by Chiral-Prep-HPLC with the following conditions: Column: CHIRALPAK AD-H SFC, 5×25 cm, 5 μm; Mobile Phase A: Hex (0.1% IPA), Mobile Phase B: EtOH; Flow rate: 20 mL/min; Gradient: 5 B to 5 B in 45 min; 254/220 nm; RT1: 19.839; RT2: 33.398. The collected fraction was concentrated under reduced pressure to give (S)—N-(5-chloro-2,3-dihydro-1H-inden-2-yl)-5-(5-(trifluoromethyl)nicotinamido)-1,2,3-thiadiazole-4-carboxamide (first eluting isomer) (3.7 mg, 4%) as a white solid and (R)—N-(5-chloro-2,3-dihydro-1H-inden-2-yl)-5-(5-(trifluoromethyl)nicotinamido)-1,2,3-thiadiazole-4-carboxamide (second eluting isomer) (5.3 mg, 5%) as a white solid.

First Eluting Isomer: $^1$H-NMR (DMSO, 400 MHz) δ (ppm): 12.64 (br s, 1H), 9.70-9.62 (m, 1H), 9.39 (s, 1H), 9.32 (s, 1H), 8.68 (s, 1H), 7.32-7.21 (m, 3H), 4.95-4.89 (m, 1H), 3.28-3.22 (m, 2H), 3.17-3.01 (m, 2H). LCMS (ES, m/z): 468 $[M+H]^+$.

Second Eluting Isomer (29): $^1$H-NMR (DMSO, 400 MHz) δ (ppm): 12.64 (br s, 1H), 9.74-9.68 (m, 1H), 9.39 (s, 1H), 9.32 (s, 1H), 8.68 (s, 1H), 7.32-7.21 (m, 3H), 4.95-4.90 (m, 1H), 3.28-3.23 (m, 2H), 3.17-3.01 (m, 2H). LCMS (ES, m/z): 468 $[M+H]^+$.

Example 7

Synthesis of 5-[2-chloro-3-(trifluoromethyl)benzamido]-N-[(4-chlorophenyl)methyl]-3-methyl-1,2-thiazole-4-carboxamide (34)

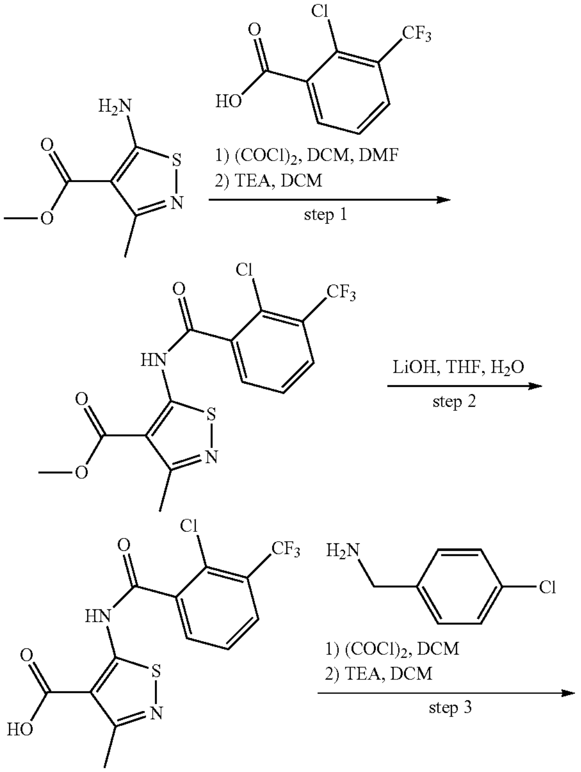

-continued

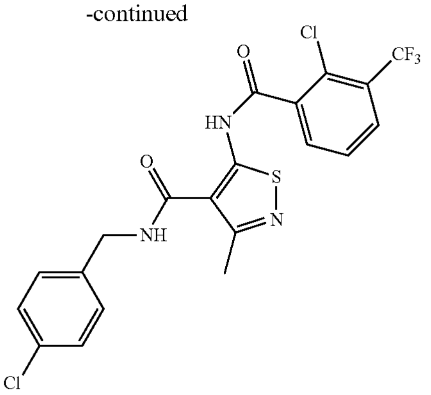

34

Step 1. methyl 5-(2-chloro-3-(trifluoromethyl)benzamido)-3-methylisothiazole-4-carboxylate To a stirred solution of 2-chloro-3-(trifluoromethyl)benzoic acid (240 mg, 1.07 mmol) in DCM (3 mL) was added $(COCl)_2$ (5 mL) and DMF (0.01 mL) dropwise at 0° C. The resulting mixture was stirred for 16 h at room temperature (25° C.). The resulting mixture was concentrated under reduced pressure. The residue was re-dissolved in DCM (5 mL). The fresh prepared acyl chloride solution was then added dropwise into a stirred mixture of methyl 5-amino-3-methylisothiazole-4-carboxylate (140 mg, 0.81 mmol) and TEA (200 μL, 1.43 mmol) in DCM (10 mL) at 0° C. The resulting mixture was stirred for 6 h at 25° C. The mixture was poured into water (10 mL) and extracted with $CH_2C_{12}$ (3×10 mL). The combined organic layers were washed with brine (15 mL), dried over anhydrous $Na_2SO_4$ and concentrated under reduced pressure. The residue was purified by Prep-TLC (eluting with 1:1 PE/EtOAc) to afford methyl 5-(2-chloro-3-(trifluoromethyl)benzamido)-3-methylisothiazole-4-carboxylate as a yellow solid (100 mg, 32%). LCMS (ES, m/z): 379,381 $[M+H]^+$.

Step 2. 5-[2-chloro-3-(trifluoromethyl)benzamido]-3-methyl-1,2-thiazole-4-carboxylic acid A mixture of methyl 5-(2-chloro-3-(trifluoromethyl)benzamido)-3-methylisothiazole-4-carboxylate (100 mg, 0.26 mmol) and LiOH (7 mg, 0.29 mmol) in THF (2 mL) and $H_2O$ (2 mL) was stirred for 16 h at 60° C. The mixture was cooled to room temperature, acidified to pH 4 with HCl (1 N) and extracted with EtOAc (3×10 mL). The combined organic layers were washed with brine (15 mL), dried over anhydrous $Na_2SO_4$ and concentrated under reduced pressure. The residue was purified by reverse flash chromatography (column, $C_{18}$ silica gel; mobile phase, ACN in water, 0% to 80% gradient in 30 min; detector, UV 254 nm). The collected fraction was concentrated to afford 5-[2-chloro-3-(trifluoromethyl)benzamido]-3-methyl-1,2-thiazole-4-carboxylic acid as a white solid (60 mg, 63%). LCMS (ES, m/z): 365,367 $[M+H]^+$.

Step 3. 5-[2-chloro-3-(trifluoromethyl)benzamido]-N-[(4-chlorophenyl)methyl]-3-methyl-1,2-thiazole-4-carboxamide (34)

To stirred solution of 5-[2-chloro-3-(trifluoromethyl)benzamido]-3-methyl-1,2-thiazole-4-carboxylic acid (40 mg, 0.11 mmol) in DCM (5 mL) was added $(COCl)_2$ (63 mg, 0.49 mmol). The reaction mixture was stirred for 5 h at 25° C. The resulting mixture was concentrated under reduced pressure. The residue was re-dissolved in DCM (3 mL), the fresh prepared acyl chloride solution was added dropwise into a stirred mixture of 1-(4-chlorophenyl)methanamine (19 mg, 0.13 mmol) and TEA (40 μL, 0.30 mmol) in DCM (5 mL) at 0° C. The resulting mixture was stirred for additional 16 h 25° C. The mixture was diluted with water (15 mL) and extracted with $CH_2Cl_2$ (3×10 mL). The combined organic layers were washed with brine (15 mL), dried over anhydrous $Na_2SO_4$ and concentrated under reduced pressure. The crude product was purified by Prep-HPLC (Column, XBridge Prep $C_{18}$ OBD Column, 19×150 mm 5 um; mobile phase, A: water (containing 0.05% TFA) and B ACN (50% up to 83% in 7 min); Detector, UV 254 nm). The collected fraction (RT: 6.54 min) was lyophilized to afford 5-[2-chloro-3-(trifluoromethyl)benzamido]-N-[(4-chlorophenyl)methyl]-3-methyl-1,2-thiazole-4-carboxamide as a white solid (28.2 mg, 52%).

$^1H$-NMR ($CD_3OD$, 400 MHz) δ (ppm): 8.02-8.00 (m, 1H), 7.95-7.93 (m, 1H), 7.69-7.65 (m, 1H), 7.39-7.34 (m, 4H), 4.56 (s, 2H), 2.57 (s, 3H). LCMS (ES, m/z): 488, 490 $[M+H]^+$.

Example 8

Synthesis of 2-[2-chloro-3-(trifluoromethyl)benzamido]-N-[(4-chlorophenyl)methyl]-4H,6H,7H-thieno[3,2-c]pyran-3-carboxamide (35)

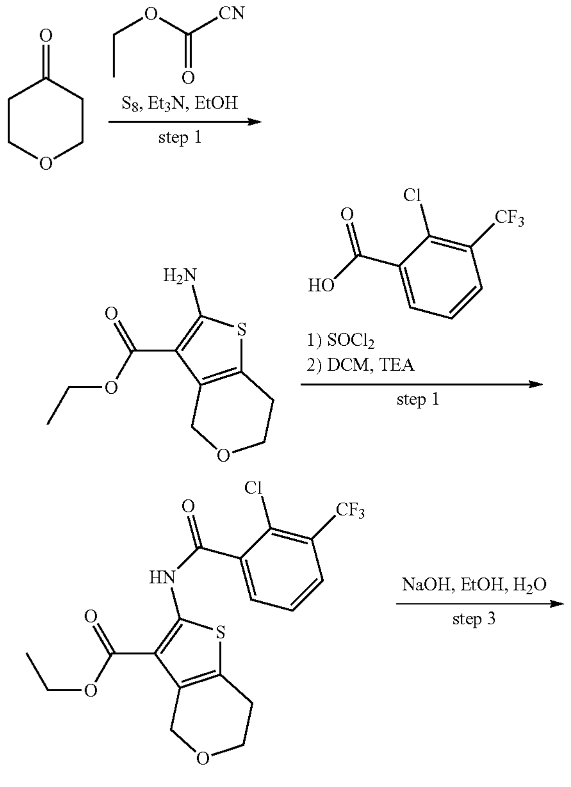

-continued

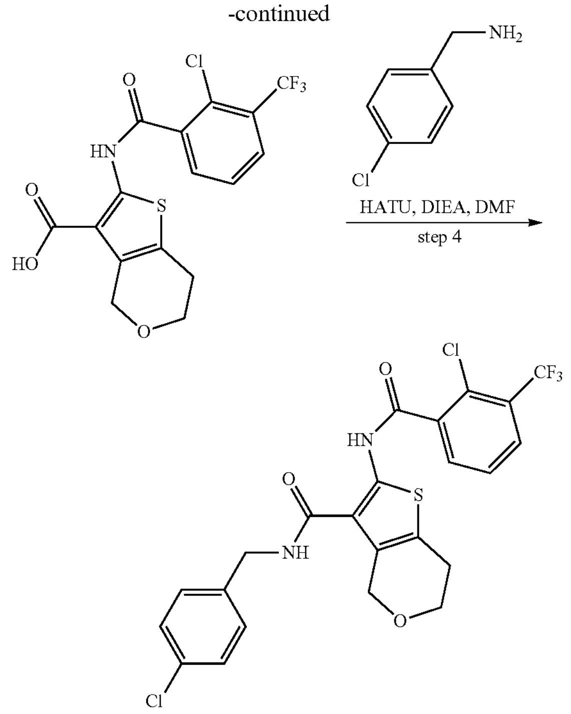

35

Step 1. ethyl 2-amino-4H,6H,7H-thieno[3,2-c]pyran-3-carboxylate

A mixture of oxan-4-one (2.84 g, 28.4 mmol) and ethyl cyanoformate (3.60 g, 34.1 mmol), TEA (6.30 mL, 43.1 mmol) and sulfur (0.90 g, 26.6 mmol) in EtOH (20 mL) was stirred for 5 h at 55° C. The reaction mixture was cooled to the room temperature, the solids were filtered out and the filtrate was concentrated under reduced pressure. The residue was purified by silica gel column chromatography, eluted with PE/EtOAc (1:1) to afford ethyl 2-amino-4H,6H,7H-thieno[3,2-c]pyran-3-carboxylate as a yellow solid (2.00 g, 31%). LCMS (ES, m/z): 228 $[M+H]^+$.

Step 2. ethyl 2-[2-chloro-3-(trifluoromethyl)benzamido]-4H,6H,7H-thieno[3,2-c]pyran-3-carboxylate A solution of 2-chloro-3-(trifluoromethyl)benzoic acid (325 mg, 1.38 mmol) and DMF (0.1 mL) in $SOCl_2$ (10 mL) was stirred for 5 h at 80° C. The mixture was cooled to room temperature and concentrated under reduced pressure. The residue was re-dissolved in DCM (5 mL). The fresh prepared acyl chloride solution was then added dropwise into a stirred mixture of ethyl 2-amino-4H,6H,7H-thieno[3,2-c]pyran-3-carboxylate (305 mg, 1.21 mmol) and TEA (335 μL, 2.42 mmol) in DCM (10 mL) at 0° C. The resulting mixture was stirred for additional 3 h at 25° C. The reaction mixture was poured into ice/water (10 mL) and extracted with $CH_2C_{12}$ (3×10 mL). The combined organic layers were washed with brine (2×5 mL), dried over anhydrous Na2SO4 and concentrated under reduced pressure. The residue was purified by Prep-TLC ($CH_2C_{12}$/MeOH 15:1) to afford ethyl 2-[2-chloro-3-(trifluoromethyl)benzamido]-4H,6H,7H-thieno[3,2-c]pyran-3-carboxylate as a yellow solid (200 mg, 38%). LCMS (ES, m/z): 434,436 $[M+H]^+$.

Step 3. 2-[2-chloro-3-(trifluoromethyl)benzamido]-4H,6H,7H-thieno[3,2-c]pyran-3-carboxylic acid A mixture of ethyl 2-[2-chloro-3-(trifluoromethyl)benzamido]-4H,6H,7H-thieno[3,2-c]pyran-3-carboxylate (200 mg, 0.46 mmol) and NaOH (33 mg, 0.83 mmol) in $H_2O$ (3 mL) and EtOH (3 mL) was stirred for 2 h at 80° C. The mixture was cooled to room temperature, acidified to pH 3 with HCl (aq. 1 N) and extracted with EtOAc (3×10 mL). The combined organic layers were washed with brine (2×5 mL), dried over anhydrous $Na_2SO_4$ and concentrated under reduced pressure to afford 2-[2-chloro-3-(trifluoromethyl) benzamido]-4H,6H,7H-thieno[3,2-c]pyran-3-carboxylic acid as a yellow solid (150 mg, 80%). LCMS (ES, m/z): 406, 408 $[M+H]^+$.

Step 4. 2-[2-chloro-3-(trifluoromethyl)benzamido]-N-[(4-chlorophenyl)methyl]-4H,6H,7H-thieno[3,2-c]pyran-3-carboxamide (35)

To the mixture of 2-[2-chloro-3-(trifluoromethyl)benzamido]-4H,6H,7H-thieno[3,2-c]pyran-3-carboxylic acid (100 mg, 0.22 mmol) and HATU (101 mg, 0.27 mmol) in DMF (3 mL) was added 1-(4-chlorophenyl)methanamine (37 mg, 0.27 mmol) and DIEA (110 μL, 0.67 mmol) at 25° C. The reaction mixture was stirred for 16 h at 25° C. The mixture was diluted with water (15 mL) and extracted with EtOAc (3×15 mL). The combined organic layers were washed with brine (15 mL), dried over anhydrous $Na_2SO_4$ and concentrated under reduced pressure. The crude product was purified by Prep-HPLC: Column, XBridge Prep $C_{18}$ OBD Column, 19×150 mm, 5 um; mobile phase, A: water (10 mmol/L $NH_4HCO_3$) and B: ACN (22% to 52% over 7 min); Detector, UV 254 nm. The product fractions (RT 6.15 min) were lyophilized to afford 2-[2-chloro-3-(trifluoromethyl)benzamido]-N-[(4-chlorophenyl)methyl]-4H,6H,7H-thieno[3,2-c]pyran-3-carboxamide as a yellow solid (8.6 mg, 7%).

$^1$H-NMR (DMSO, 400 MHz) δ (ppm): 11.80 (s, 1H), 8.30-8.27 (m, 1H), 8.03 (d, J=8.0 Hz, 1H), 7.93 (d, J=7.6 Hz, 1H), 7.72-7.68 (m, 1H), 7.38-7.32 (m, 4H), 4.71 (s, 2H), 4.41 (d, J=6.4 Hz, 2H), 3.89-3.87 (m, 2H), 2.80 (s, 2H). LCMS (ES, m/z): 529,531 $[M+H]^+$.

Example 9

USP 36 Inhibition Biochemical Assay Protocol

USP36 enzymatic assays were performed in a final volume of 6 μL in buffer containing 20 mM Tris-HCl pH 8.0, (Corning 46-031-CM), 3 mM 2-Mercaptoethanol (Sigma, M6250), 0.03% BGG (Sigma, G7516), and 0.01% Triton X-100 (Sigma, 93443). Test compounds were serially diluted in DMSO (Sigma, G7516) to obtain 10-point, 3-fold series. Nanoliter quantities were pre-dispensed into 1536 assay plates (Corning, 9110BC) for the concentration response range, 26.6 μM to 1.35 nM. 3 μL of 2× enzyme was added to the assay plates, preincubated with compound for 30 minutes and then 3 μL of 2× substrate was added to initiate the reaction (2 nM human USP36 (81-461) and 25 nM Ub-Rh110MP (UbiQ, UbiQ-126) final concentrations). Enzyme and substrate concentrations and incubation times were optimized for the maximal signal-to-background while maintaining linear initial velocity conditions at a fixed substrate concentration below Km.

Fluorescence signal was measured on an EnVision Plate Reader (PerkinElmer) equipped with 485 nm excitation filter and 535 nm emission filters. Measurements were taken at 2.5 minutes intervals for 10 minutes, curves were shown to progress linearly.

Rates were calculated by: rate=((final FLU−initial FLU)/600 seconds) where final FLU=fluorescence at time 10 minutes, initial FLU=fluorescence at time 0 minutes and 600=duration of reaction in seconds.

Data were reported as percent inhibition compared with control wells based on the following equation: % inh=100*((rate−AveLow)/(AveHigh−AveLow)) where rate=measured rate of fluorescence generated during assay, AveLow=average rate of no enzyme control (n=32), and AveHigh=average rate of DMSO control (n=32).

$IC_{50}$ values were determined by curve fitting of the standard 4 parameter logistic fitting algorithm included in the Activity Base software package (IDBS) using XE Designer equation Model 205. Data were fitted using the Levenburg Marquardt algorithm. $IC_{50}$ values for specific embodied compounds are reported in Table A.

TABLE A

| Compound Number | Structure and Name | USP 36 $IC_{50}$ (μM) |
|---|---|---|
| 1 | 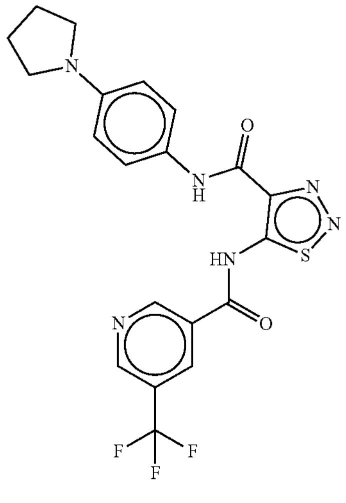 N-(4-(pyrrolidin-1-yl)phenyl)-5-(5-(trifluoromethyl)nicotinamido)-1,2,3-thiadiazole-4-carboxamide | 0.1982 |

TABLE A-continued
| Compound Number | Structure and Name | USP 36 $IC_{50}$ (μM) |
| --- | --- | --- |
| 2 | 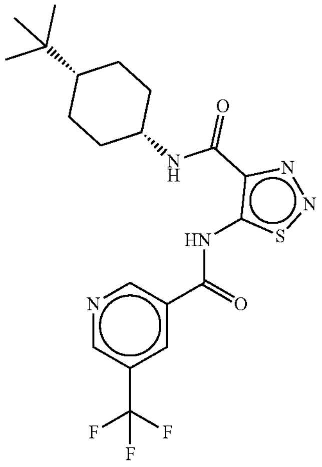 N-((1s,4s)-4-(tert-butyl)cyclohexyl)-5-(5-(trifluoromethyl)nicotinamido)-1,2,3-thiadiazole-4-carboxamide | 0.329 |
| 3 | 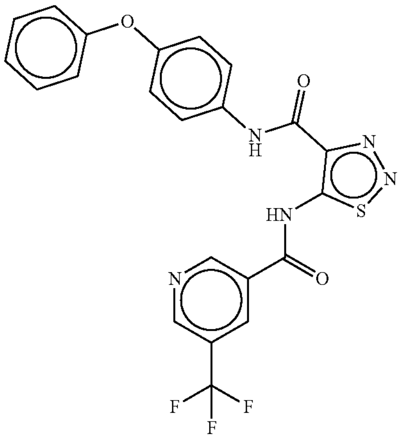 N-(4-phenoxyphenyl)-5-(5-(trifluoromethyl)nicotinamido)-1,2,3-thiadiazole-4-carboxamide | 0.335 |

TABLE A-continued
| Compound Number | Structure and Name | USP 36 $IC_{50}$ (μM) |
| --- | --- | --- |
| 4 | 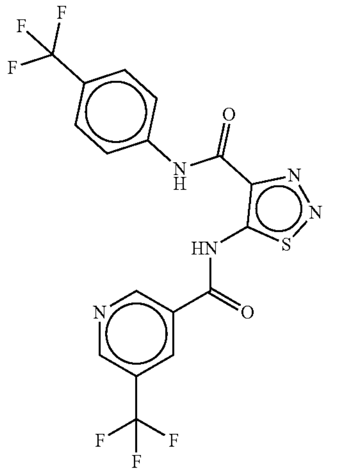 5-(5-(trifluoromethyl)nicotinamido)-N-(4-(trifluoromethyl)phenyl)-1,2,3-thiadiazole-4-carboxamide | 0.34 |
| 5 | 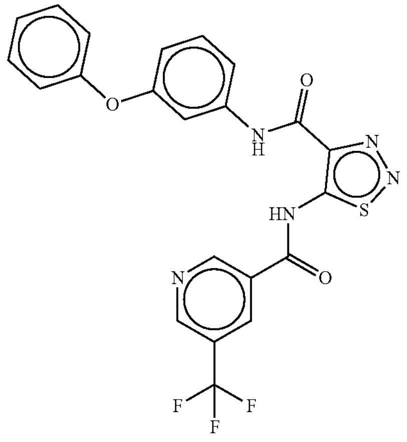 N-(3-phenoxyphenyl)-5-(5-(trifluoromethyl)nicotinamido)-1,2,3-thiadiazole-4-carboxamide | 0.365 |
| 6 | 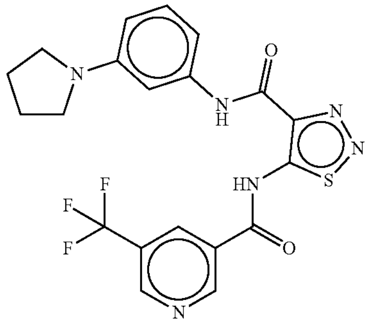 N-(3-(pyrrolidin-1-yl)phenyl)-5-(5-(trifluoromethyl)nicotinamido)-1,2,3-thiadiazole-4-carboxamide | 0.407 |

TABLE A-continued
| Compound Number | Structure and Name | USP 36 $IC_{50}$ (μM) |
|---|---|---|
| 7 | 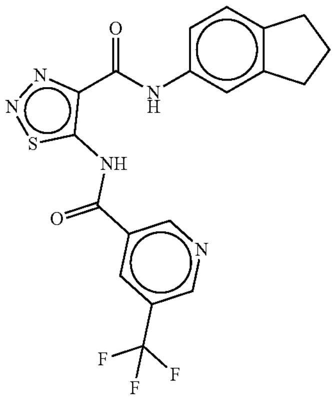 N-(2,3-dihydro-1H-inden-5-yl)-5-(5-(trifluoromethyl)nicotinamido)-1,2,3-thiadiazole-4-carboxamide | 0.507 |
| 8 | 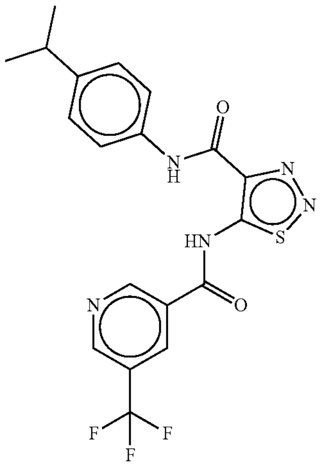 N-(4-isopropylphenyl)-5-(5-(trifluoromethyl)nicotinamido)-1,2,3-thiadiazole-4-carboxamide | 0.553 |
| 9 | 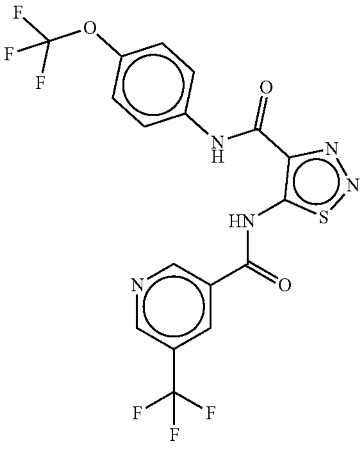 N-(4-(trifluoromethoxy)phenyl)-5-(5-(trifluoromethyl)nicotinamido)-1,2,3-thiadiazole-4-carboxamide | 0.556 |

TABLE A-continued
| Compound Number | Structure and Name | USP 36 $IC_{50}$ (μM) |
|---|---|---|
| 10 | 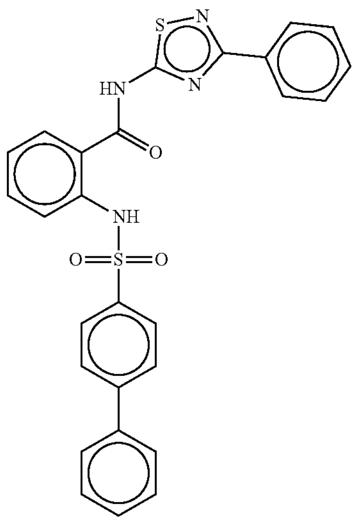 2-([1,1'-biphenyl]-4-sulfonamido)-N-(3-phenyl-1,2,4-thiadiazol-5-yl)benzamide | 0.56 |
| 11 | 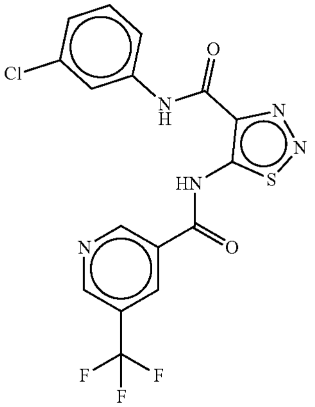 N-(3-chlorophenyl)-5-(5-(trifluoromethyl)nicotinamido)-1,2,3-thiadiazole-4-carboxamide | 0.587 |
| 12 | 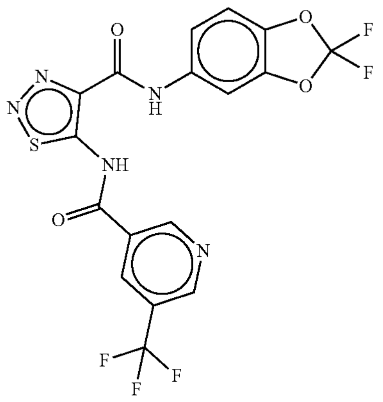 N-(2,2-difluorobenzo[d][1,3]dioxol-5-yl)-5-(5-(trifluoromethyl)nicotinamido)-1,2,3-thiadiazole-4-carboxamide | 0.666 |

TABLE A-continued
| Compound Number | Structure and Name | USP 36 $IC_{50}$ (μM) |
| --- | --- | --- |
| 13 | 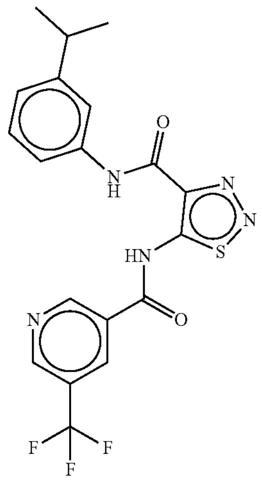 N-(3-isopropylphenyl)-5-(5-(trifluoromethyl)nicotinamido)-1,2,3-thiadiazole-4-carboxamide | 0.669 |
| 14 | 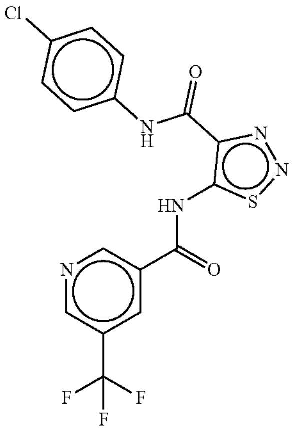 N-(4-chlorophenyl)-5-(5-(trifluoromethyl)nicotinamido)-1,2,3-thiadiazole-4-carboxamide | 0.689 |

TABLE A-continued
| Compound Number | Structure and Name | USP 36 $IC_{50}$ (μM) |
| --- | --- | --- |
| 15 | 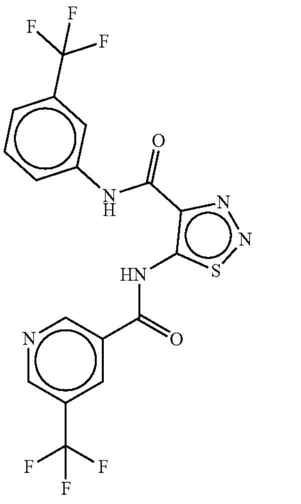 5-(5-(trifluoromethyl)nicotinamido)-N-(3-(trifluoromethyl)phenyl)-1,2,3-thiadiazole-4-carboxamide | 0.749 |
| 16 | 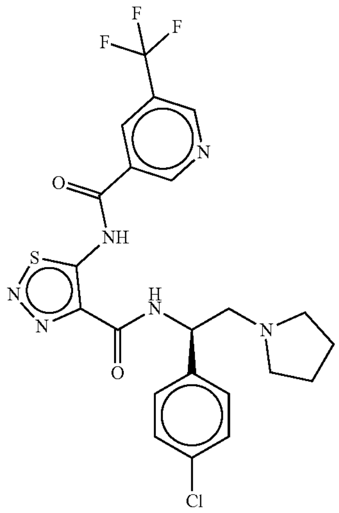 (R)-N-(1-(4-chlorophenyl)-2-(pyrrolidin-1-yl)ethyl)-5-(5-(trifluoromethyl)nicotinamido)-1,2,3-thiadiazole-4-carboxamide | 0.764 |

TABLE A-continued
| Compound Number | Structure and Name | USP 36 $IC_{50}$ (μM) |
|---|---|---|
| 17 | 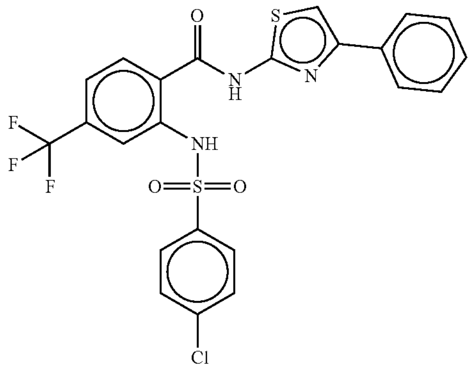 2-((4-chlorophenyl)sulfonamido)-N-(4-phenylthiazol-2-yl )-4-(trifluoromethyl)benzamide | 0.816 |
| 18 | 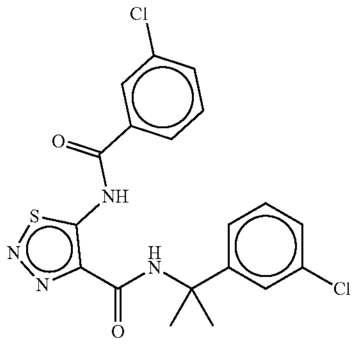 5-(3-chlorobenzamido)-N-(2-(3-chlorophenyl)propan-2-yl)-1,2,3-thiadiazole-4-carboxamide | 0.82 |
| 19 | 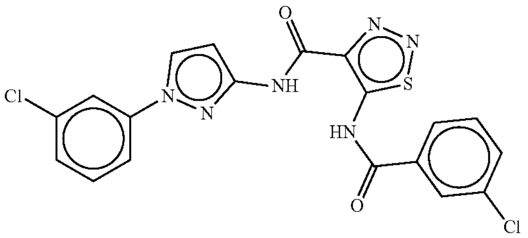 5-(3-chlorobenzamido)-N-(1-(3-chlorophenyl)-1H-pyrazol-3-yl)-1,2,3-thiadiazole-4-carboxamide | 0.826 |

TABLE A-continued
| Compound Number | Structure and Name | USP 36 $IC_{50}$ (μM) |
| --- | --- | --- |
| 20 | 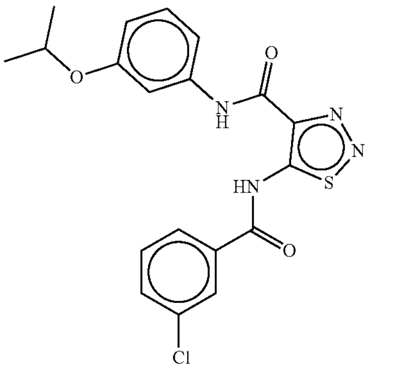 5-(3-chlorobenzamido)-N-(3-isopropoxyphenyl)-1,2,3-thiadiazole-4-carboxamide | 0.849 |
| 21 | 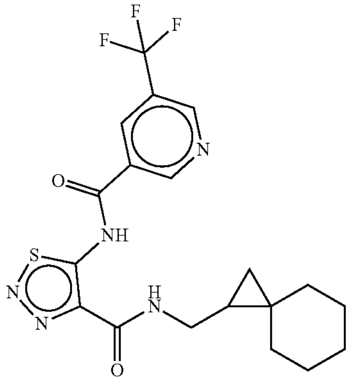 N-(spiro[2.5]octan-1-ylmethyl)-5-(5-(trifluoromethyl)nicotinamido)-l,2,3-thiadiazole-4-carboxamide | 0.868 |
| 22 | 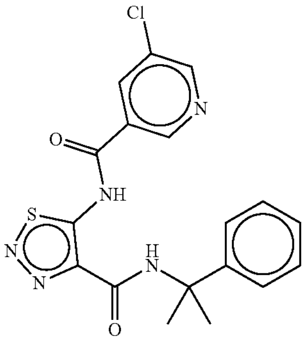 5-(3-chlorobenzamido)-N-(2-phenylpropan-2-yl)-1,2,3-thiadiazole-4-carboxamide | 0.898 |

TABLE A-continued
| Compound Number | Structure and Name | USP 36 $IC_{50}$ (μM) |
| --- | --- | --- |
| 23 | 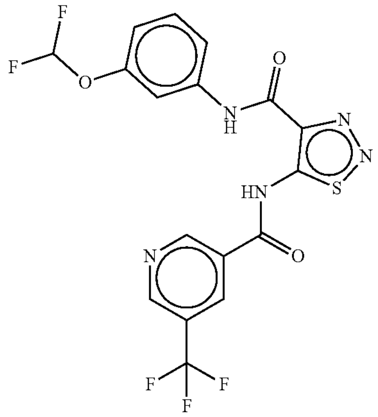 N-(3-(difluoromethoxy)phenyl)-5-(5-(trifluoromethyl)nicotinamido)-1,2,3-thiadiazole-4-carboxamide | 0.9 |
| 24 | 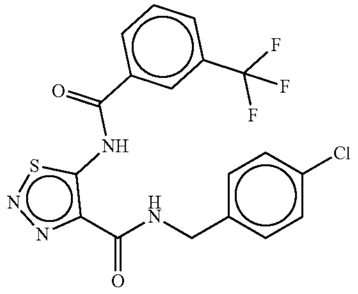 N-(4-chlorobenzyl)-5-(3-(trifluoromethyl)benzamido)-1,2,3-thiadiazole-4-carboxamide | 0.923 |
| 25 | 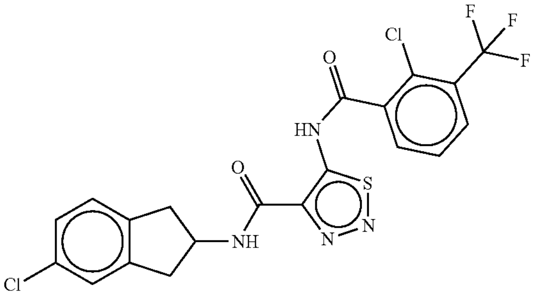 N-(5-chloro-2,3-dihydro-1H-inden-2-yl)-5-(2-chloro-3-(trifluoromethyl)benzamido)-1,2,3-thiadiazole-4-carboxamide | 0.961 |

TABLE A-continued
| Compound Number | Structure and Name | USP 36 IC$_{50}$ (μM) |
| --- | --- | --- |
| 26 | 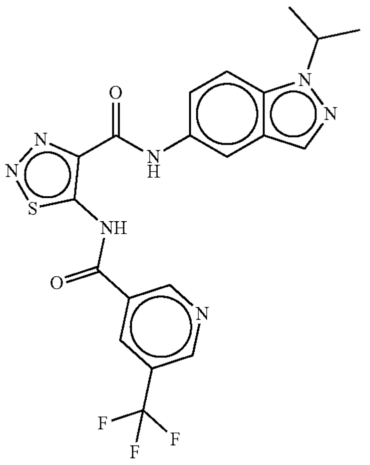 N-(1-isopropyl-1H-indazol-5-yl)-5-(5-(trifluoromethyl)nicotinamido)-1,2,3-thiadiazole-4-carboxamide | 0.961 |
| 27 | 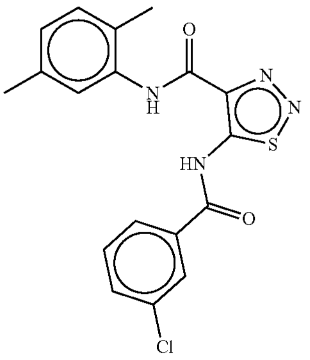 5-(3-chlorobenzamido)-N-(2,5-dimethylphenyl)-1,2,3-thiadiazole-4-carboxamide | 0.964 |
| 28 | 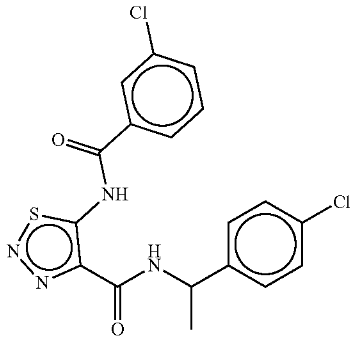 5-(3-chlorobenzamido)-N-(1-(4-chlorophenyl)ethyl)-1,2,3-thiadiazole-4-carboxamide | 0.989 |

TABLE A-continued
| Compound Number | Structure and Name | USP 36 $IC_{50}$ (μM) |
|---|---|---|
| 29 | 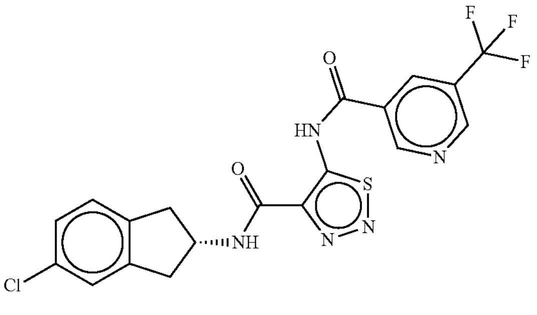 (S)-N-(5-chloro-2,3-dihydro-1H-inden-2-yl)-5-(5-(trifluoromethyl)nicotinamido)-1,2,3-thiadiazole-4-carboxamide | 1.011 |
| 30 | 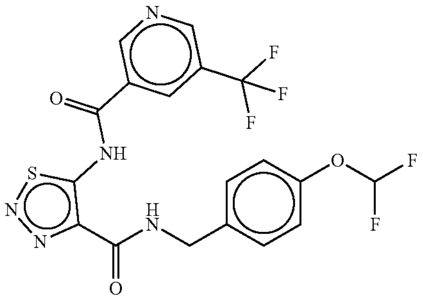 N-(4-(difluoromethoxy)benzyl)-5-(5-(trifluoromethyl)nicotinamido)-1,2,3-thiadiazole-4-carboxamide | 1.011 |
| 31 | 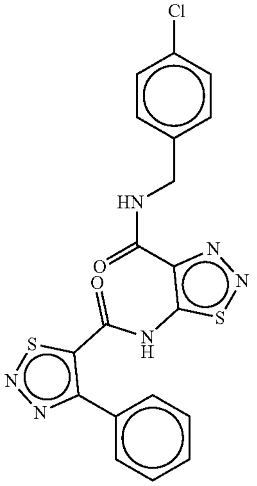 N-(4-chlorobenzyl)-5-(4-phenyl-1,2,3-thiadiazole-5-carboxamido)-1,2,3-thiadiazole-4-carboxamide | 1.046 |

TABLE A-continued
| Compound Number | Structure and Name | USP 36 $IC_{50}$ (μM) |
|---|---|---|
| 32 | 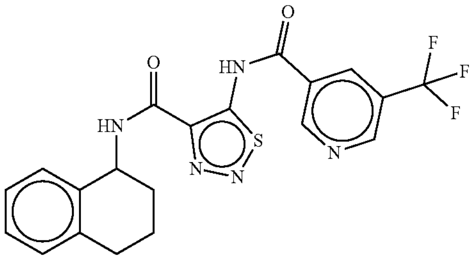 N-(1,2,3,4-tetrahydronaphthalen-1-yl)-5-(5-(trifluoromethyl)nicotinamido)-1,2,3-thiadiazole-4-carboxamide | 1.046 |
| 33 | 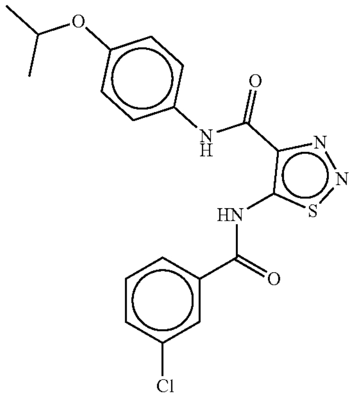 5-(3-chlorobenzamido)-N-(4-isopropoxyphenyl)-1,2,3-thiadiazole-4-carboxamide | 1.078 |
| 34 | 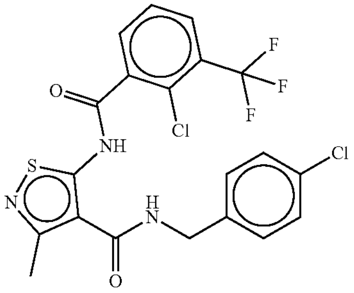 5-(2-chloro-3-(trifluoromethyl)benzamido)-N-(4-chlorobenzyl)-3-methylisothiazole-4-carboxamide | 1.627 |

TABLE A-continued

| Compound Number | Structure and Name | USP 36 $IC_{50}$ (μM) |
| --- | --- | --- |
| 35 | 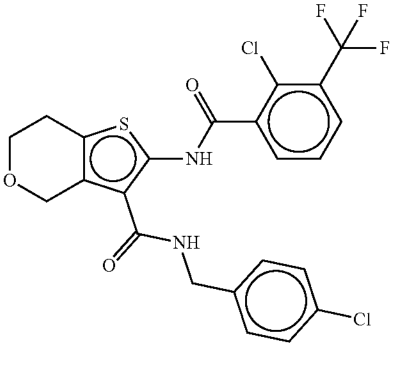 2-(2-chloro-3-(trifluoromethyl)benzamido)-N-(4-chlorobenzyl)-6,7-dihydro-4H-thieno[3,2-c]pyran-3-carboxamide | 9.56 |

The present disclosure enables one of skill in the relevant art to make and use the inventions provided herein in accordance with multiple and varied embodiments. Various alterations, modifications, and improvements of the present disclosure that readily occur to those skilled in the art, including certain alterations, modifications, substitutions, and improvements are also part of this disclosure. Accordingly, the foregoing description are by way of example to illustrate the discoveries provided herein. Furthermore, the foregoing Description and Examples are exemplary of the present invention and not limiting thereof. The scope of the invention is therefore set out in the appended claims.

We claim:

1. A compound of formula (II):

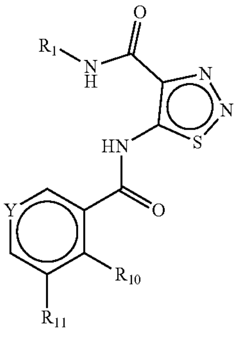

(II)

or a pharmaceutically acceptable salt thereof, wherein:

Y is N or CH;

$R_1$ is selected from:

($C_1$-$C_4$) alkyl optionally substituted with 1-3 $R_2$, ($C_3$-$C_6$) cycloalkyl optionally substituted with one $R_3$, aryl optionally substituted with 1-2 $R_4$, heteroaryl substituted with one $R_5$, bicyclic heteroaryl optionally substituted with one ($C_1$-$C_4$) alkyl, partially saturated bicyclyl optionally substituted with one halogen, and

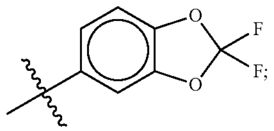

each $R_2$ is independently selected from:

($C_1$-$C_4$) alkyl, ($C_3$-$C_6$) cycloalkyl, ($C_6$-$C_{12}$) spirocycloalkyl, aryl optionally substituted with one halogen or —$OR_6$, and 3-6 membered heterocyclyl;

$R_3$ is ($C_1$-$C_4$) alkyl;

each $R_4$ is independently selected from ($C_1$-$C_4$) alkyl optionally substituted with halogen, —$OR_6$, halogen, and 3-6 membered heterocyclyl;

$R_5$ is aryl substituted with one halogen;

$R_6$ is selected from aryl, and ($C_1$-$C_4$) alkyl optionally substituted with halogen;

$R_{10}$ is hydrogen or halogen; and $R_{11}$ is halogen or ($C_1$-$C_4$) alkyl substituted with halogen.

2. The compound of claim 1, wherein $R_2$ is selected from the group consisting of: methyl, cyclopropyl fused to cyclohexyl, pyrrolidinyl, and phenyl optionally substituted with one-$C_1$.

3. The compound of claim 1, wherein $R_3$ is tert-butyl.

4. The compound of claim 1, wherein $R_4$ is selected from the group consisting of: methyl, isopropyl, trifluoromethyl, —Cl, and pyrrolidinyl.

5. The compound of claim 1, wherein $R_5$ is phenyl substituted with one —Cl.

6. The compound of claim 1, wherein $R_6$ is selected from the group consisting of: phenyl, isopropyl, difluoromethyl, and trifluoromethyl.

7. The compound of claim 1, wherein $R_{10}$ is hydrogen or —Cl.

8. The compound of claim 1, wherein $R_{11}$ is —Cl or trifluoromethyl.

9. The compound of claim 1, selected from the group consisting of:

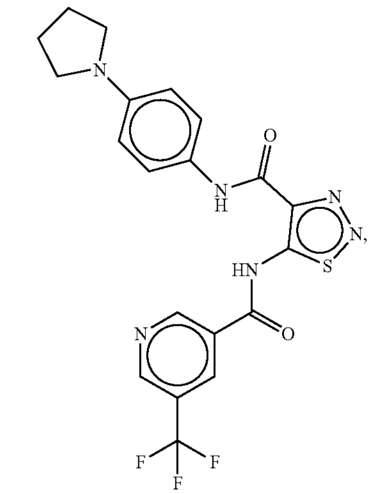
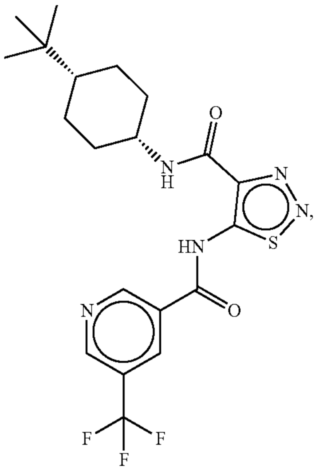
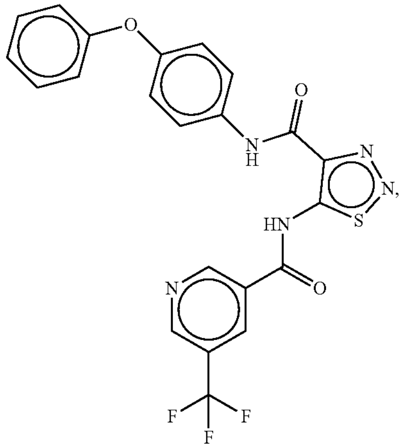
-continued
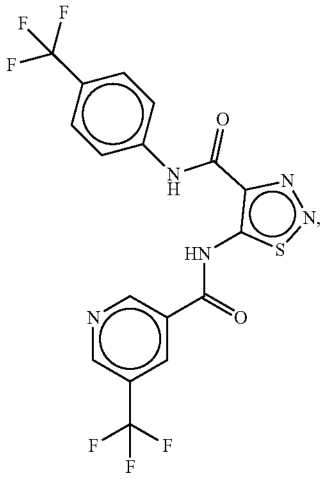
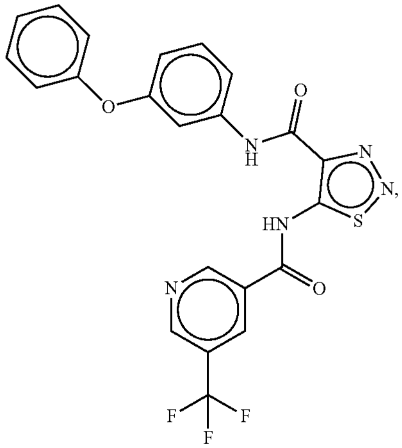
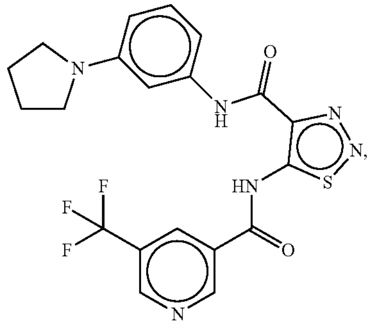
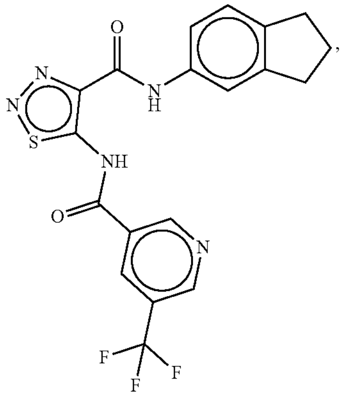

-continued
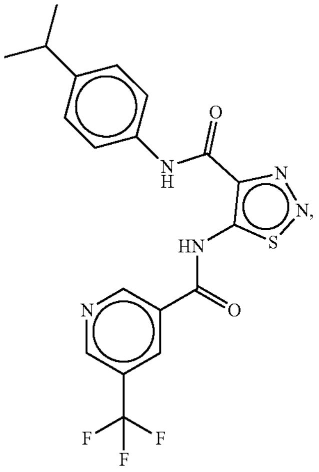
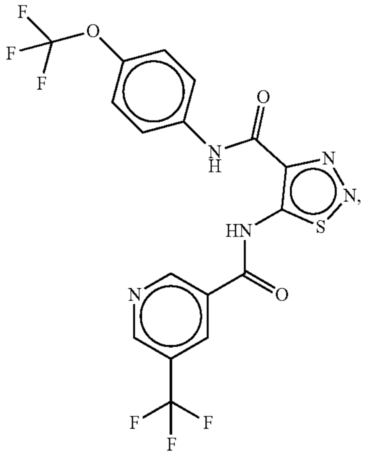
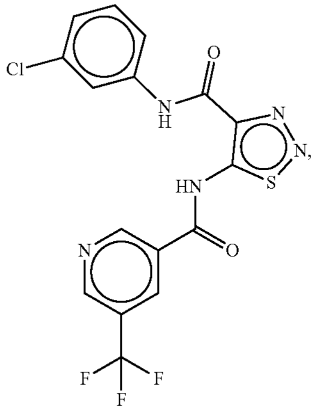
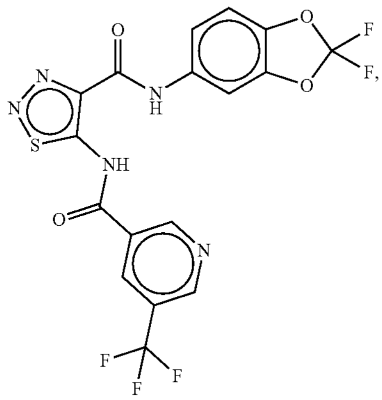
-continued
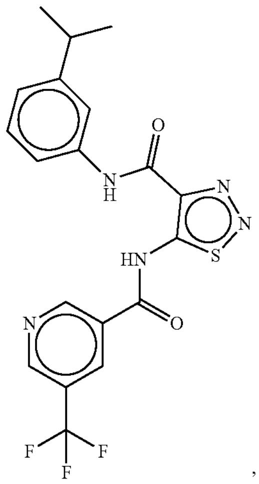
,
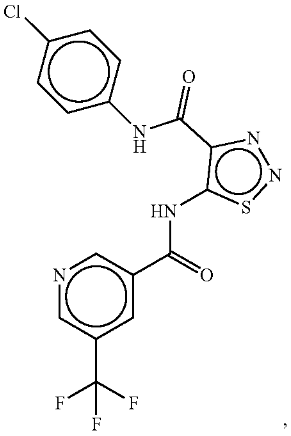
,
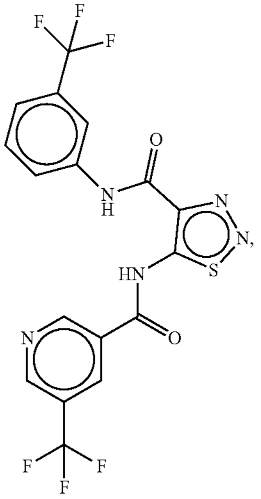
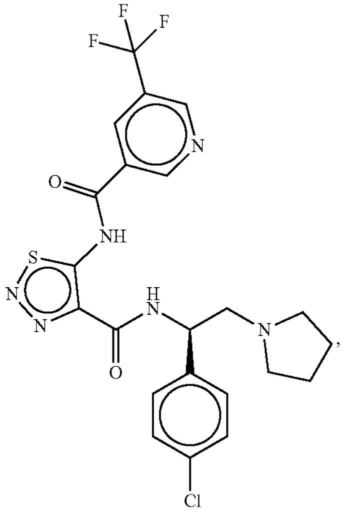

-continued
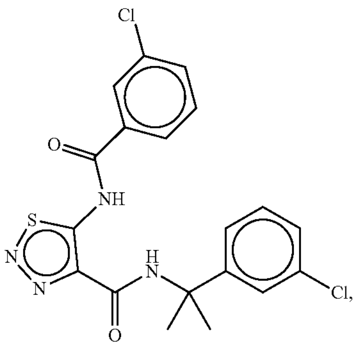
,
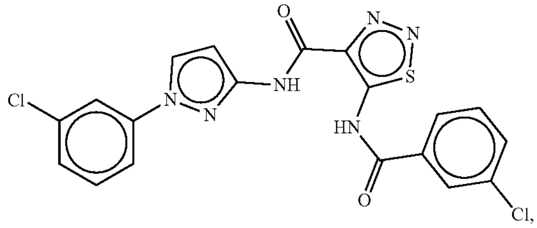
,
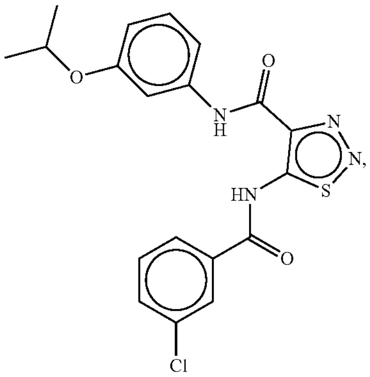
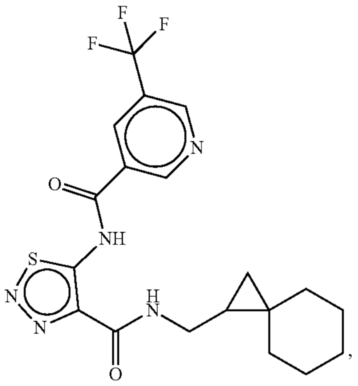
,
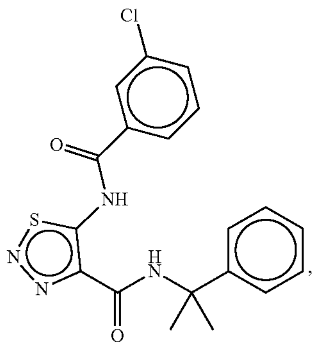
,
-continued
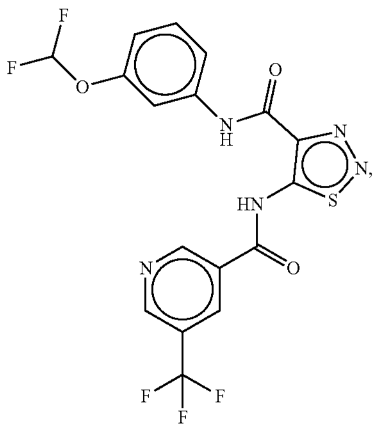
,
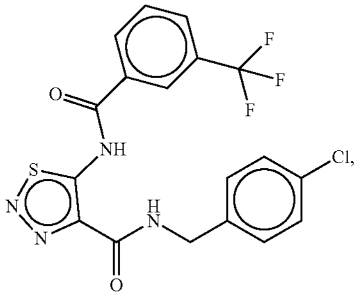
,
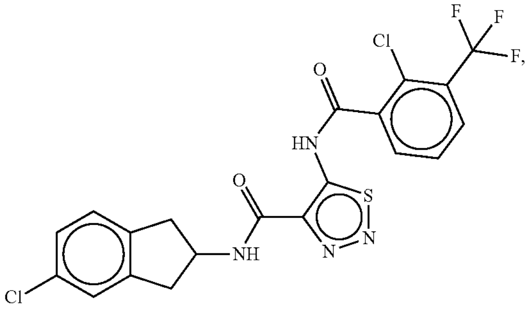
,
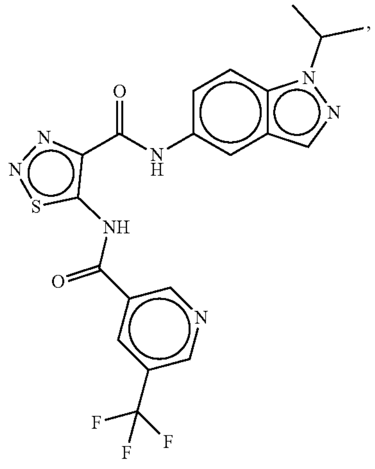
, -continued

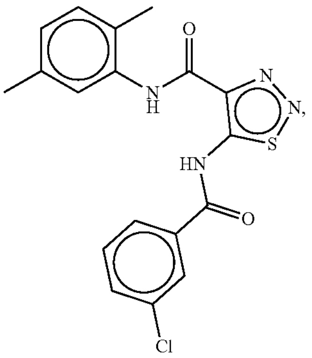

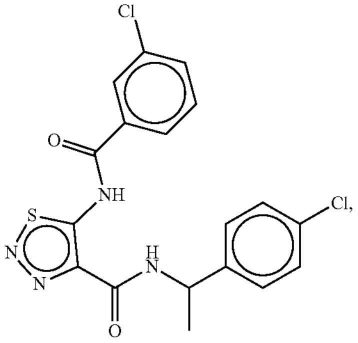

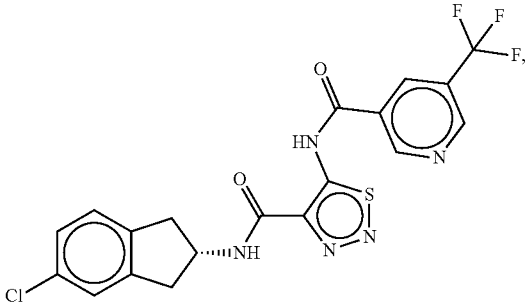

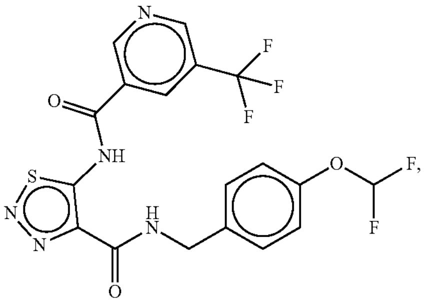

-continued

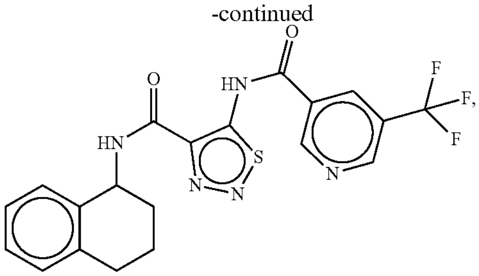

and

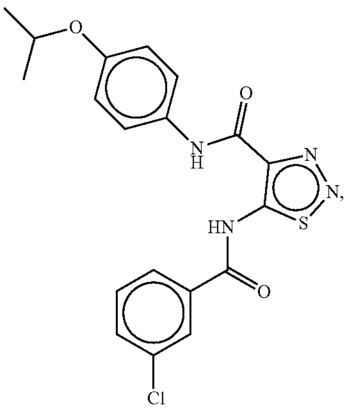

or a pharmaceutically acceptable salt thereof.

10. A pharmaceutical composition comprising the compound of claim 1 and one or more of a pharmaceutically acceptable carrier, adjuvant, or vehicle.

11. A method of treating, preventing, inhibiting, or eliminating a disease or disorder associated with the activity of USP36 in a patient comprising: administering to the patient in need thereof, a therapeutically effective amount of the compound of claim 1, wherein the disease or disorder is cancer.

* * * * *